United States Patent
Moore, II et al.

(10) Patent No.: US 8,431,595 B2
(45) Date of Patent: Apr. 30, 2013

(54) FURANOPYRIDINE CANNABINOID COMPOUNDS AND RELATED METHODS OF USE

(75) Inventors: Bob M. Moore, II, Nesbit, MS (US); Steven Gurley, Memphis, TN (US); Suni Mustafa, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 189 days.

(21) Appl. No.: 12/860,733

(22) Filed: Aug. 20, 2010

(65) Prior Publication Data

US 2011/0046176 A1 Feb. 24, 2011

Related U.S. Application Data

(60) Provisional application No. 61/235,502, filed on Aug. 20, 2009.

(51) Int. Cl.
*A61K 31/4355* (2006.01)
*C07D 471/06* (2006.01)

(52) U.S. Cl.
USPC .......................................... 514/302; 546/116

(58) Field of Classification Search ............... 514/302; 546/116
See application file for complete search history.

(56) References Cited

FOREIGN PATENT DOCUMENTS

| WO | 02-100857 | | 12/2002 |
|---|---|---|---|
| WO | 03-022856 | A1 | 3/2003 |
| WO | 03-029252 | A1 | 4/2003 |

*Primary Examiner* — Taofiq A Solola
(74) *Attorney, Agent, or Firm* — Reinhart Boerner Van Deuren s.c.

(57) ABSTRACT

Furanopyridine cannabinoid analog compounds of the formula I are disclosed.

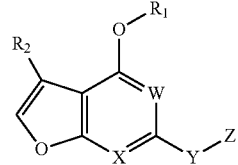

The compounds are useful to modify the activity of CB1 and CB2 receptors and treat conditions mediated by these receptors.

17 Claims, 13 Drawing Sheets

FURANOPYRIDINE CANNABINOID COMPOUNDS AND RELATED METHODS OF USE

This application claims priority benefit from application Ser. No. 61/235,502 filed Aug. 20, 2009, incorporated herein by reference in its entirety.

FIELD OF THE INVENTION

The present invention relates generally to certain non-classical furanopyridine cannabinoid compounds. The compounds are useful for the treatment of cannabinoid receptor-mediated condition, such as, for example, cancer and the like. The present invention also relates to pharmaceutical preparations employing such compounds and methods of administering and/or using therapeutically effective amounts of such analogs to provide a physiological effect.

BACKGROUND OF THE INVENTION

The classical cannabinoid, delta-9-tetrahydrocannabinol ($\Delta^9$-THC), is the major active constituent extracted from *Cannabis sativa*. The effects of cannabinoids are due to an interaction with specific high-affinity receptors. Presently, two cannabinoid receptors have been characterized: CB-1, a central receptor found in the mammalian brain and a number of other sites in the peripheral tissues; and CB-2, a peripheral receptor found principally in cells related to the immune system. In addition, it has recently been reported that the GPR35, GPR55, and GPR119 orphan receptors either bind cannabinoid-type ligands or possess high sequence homology to established receptors and, as such, have been proposed as new receptor subtypes. The CB-1 receptor is believed to mediate the psychoactive properties associated with classical cannabinoids. Characterization of these receptors has been made possible by the development of specific synthetic ligands such as the agonists WIN 55212-2 and CP 55,940 (D'Ambra et al., *J. Med. Chem.* 35:124 (1992)) and CP 55,940 (Melvin et al., *Med. Chem.* 27:67 (1984)).

Pharmacologically, cannabinoids can be used to affect a variety of targets such as the central nervous system, the cardiovascular system, the immune system and/or endocrine system. More particularly, compounds possessing an affinity for either the CB-1 or the CB-2 cannabinoid and potentially the GPR35, GPR55, and GPR119 receptors can act on the central nervous system and immunomodulators. In addition, these compounds are useful as anticancer agents, antiobesity agents, analgesics, myorelaxation agents and antiglaucoma agents. Such compounds can also be used for the treatment of thymic disorders, vomiting; various types of neuropathy, memory disorders, dyskinesia, migraine, multiple sclerosis; asthma, epilepsy, ischemia, angor, orthostatic hypotension, osteoporosis, liver fibrosis, inflammation and irritable bowel disease, diabetes, and cardiac insufficiency.

However, certain cannabinoids such as $\Delta^9$-THC also affect cellular membranes, producing undesirable side effects such as drowsiness, impairment of monoamine oxidase function, and impairment of non-receptor mediated brain function. The addictive and psychotropic properties of some cannabinoids tend to limit their therapeutic value.

There still remains an ongoing need in the art for compounds, whether classical or non-classical cannabinoid analogs, that can be used for therapeutic purposes to affect treatment of conditions or disorders that are mediated by any one of or any combination of the CB-1 receptor, the CB-2 receptor, the GPR55 receptor, the GPR35 receptor, and the GPR119 receptor.

SUMMARY OF THE INVENTION

In light of the foregoing, it is an object of the present invention to provide a range of furanopyridine cannabinoid analog compounds, compositions and/or related methods, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to identify one or more classes of cannabinoid compounds exhibiting affinity for cannabinoid and related receptors found in human cells and tissues.

It is also an object of the present invention to provide one or more furanopyridine non-classical cannabinoid receptor ligands comprising a furanopyridine ring system.

It can be another object of the present invention to identify such compounds exhibiting cannabinoid receptor selectivity, for directed therapeutic use.

Other objects, features, benefits and advantages of the present invention will be apparent from this summary and the following descriptions of certain embodiments, and will be readily apparent to those skilled in the art having knowledge of various cannabinoid compound and related therapeutic methods. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a cannabinoid analog compound selected from compounds of a formula (I) below.

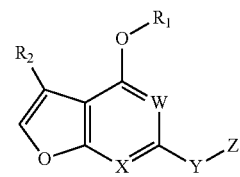

wherein one of W and X can be N and the other can be C; Y can be selected from S, O, $CH_2$, $CH(CH_3)$, $CH(OH)$, $C(CH_3)(OH)$, $C(CH_3)_2$, $C(-U(CH_2)_nU-)$, $C((CH_2)_nCH_3)_2$, $C(O)$, $NH$, $S(O)$, $S(O)_2$, $C(O)NH$, $S(O)NH$ and $S(O)_2NH$; U can be selected from $CH_2$, S, and O; n can be an integer $\geq 1$, and preferably from 1 to 6; Z can be selected from alkyl, cycloalkyl, aryl, mono-, di-, and trisubstituted aryl, heteroaryl, mono-, di-, and trisubstituted heteroaryl, arylalkyl, and mono-, di-, and trisubstituted arylalkyl; $R_1$ can be selected from H, $CH_3$, $CH_2CH_3$, aminoalkyl, morpholinoalkyl, and hemisuccinates; and $R_2$ can be selected from H, substituted and unsubstituted alkyl, substituted and unsubstituted cycloalkyl, substituted and unsubstituted aryl, substituted and unsubstituted heteroaryl, substituted and unsubstituted heterocycloalkyl, and arylalkyl, cycloalkylalkyl, heterocycloalkylalkyl and heteroarylalkyl, wherein each alkyl portion can be optionally substituted up to three times and the ring portion of each can be optionally substituted with one, two, three, four or five substituents.

In part, the present invention can be directed to a salt of a compound in accordance herewith.

The present invention can be directed to a pro-drug of a compound in accordance herewith.

In part, the present invention can also be directed to a pharmaceutical composition comprising a compound of the sort described herein, a salt and/or a pro-drug thereof; and a pharmaceutically acceptable carrier component.

The present invention can also be directed to a method of modifying the activity of a cannabinoid receptor. Such a method can comprise providing a compound, salt and/or pro-drug of the present invention or any other compound disclosed herein that has activity at a cannabinoid or related receptor, a salt and/or pro-drug thereof; and contacting a cell and/or cannabinoid receptor of a cell with such a compound. As illustrated below, such contact can be at least partially sufficient to at least partially modify activity of such a cannabinoid receptor.

In part, the present invention can also be directed to a method of treating a cannabinoid receptor-mediated condition. Such a method can comprise providing a compound in accordance herewith or any other compound disclosed herein that has activity at a cannabinoid receptor, a salt and/or pro-drug thereof; and administering to a patient an amount of such a compound, salt and/or pro-drug, that is at least partially effective to treat a cannabinoid receptor-mediated condition. This aspect of the invention can relate to the use of agonists of a CB-1 or a related receptor, antagonists of a CB-1 or related receptor, agonists of a CB-2 or related receptor, and/or antagonists of a CB-2 or related receptor to treat or prevent disease conditions mediated by hyperactivity of CB-1 and/or CB-2 (or related) receptors or either inactivity or hypoactivity of the CB-1 and/or CB-2 (or related) receptors.

In part, the present invention can also be directed to a compound selected from compounds of a formula I:

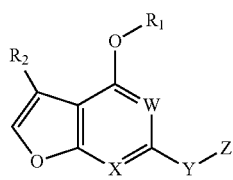

wherein one of W and X can be N and the other can be C; $R_2$ can be selected from substituted and unsubstituted phenyl and substituted and unsubstituted thiophenyl; $R_1$ can be selected from H, alkyl, aminoalkyl, morpholinoalkyl, and hemisuccinate; Y can be selected from carbonyl, dimethylmethylene and hydroxymethylene; and Z can be selected from substituted and unsubstituted alkyl, phenyl, substituted phenyl, cycloalkyl, substituted cycloalkyl, thiophenyl and substituted thiophenyl, such substituents as would be understood by those skilled in the art made aware of this invention, including but not limited to those described elsewhere herein. In certain embodiments, Z can be an alkyl, phenyl, thiophenyl or a cycloalkyl moiety and, optionally, Y can be a dimethylmethylene or carbonyl moiety. Regardless, such a compound can be selected from salts and/or pro-drugs of such a compound.

Without limitation, this invention can also be directed to a method of cancer treatment. Such a method can comprise providing a cancer cell comprising a cannabinoid receptor, such a cell of a growth of cancer cells; and contacting such a growth with a cannabinoid compound selected from compounds of a formula

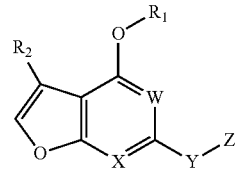

wherein one of W and X can be N and the other can be C; Y can be selected from S, O, $CH_2$, $CH(CH_3)$, $CH(OH)$, $C(CH_3)(OH)$, $C(CH_3)_2$, $C(-U(CH_2)_nU-)$, $C((CH_2)_nCH_3)_2$, $C(O)$, NH, $S(O)$, $S(O)_2$, $C(O)NH$, $S(O)NH$ and $S(O)_2NH$; U can be selected from $CH_2$, S, and O; n can be an integer $\geq 1$, and preferably from 1 to 6; Z can be selected from alkyl, cycloalkyl, aryl, mono-, di-, and trisubstituted aryl, heteroaryl, mono-, di-, and trisubstituted heteroaryl, arylalkyl, and mono-, di-, and trisubstituted arylalkyl; $R_1$ can be selected from H, $CH_3$, $CH_2CH_3$, aminoalkyl, morpholinoalkyl, and hemisuccinates; and $R_2$ can be selected from H, substituted and unsubstituted alkyl, substituted and unsubstituted cycloalkyl, substituted and unsubstituted aryl, substituted and unsubstituted heteroaryl, substituted and unsubstituted heterocycloalkyl, and arylalkyl, cycloalkylalkyl, heterocycloalkylalkyl and heteroarylalkyl, wherein each alkyl portion can be optionally substituted up to three times and the ring portion of each can be optionally substituted with one, two, three, four or five substituents; and salts and pro-drugs of said compounds, and combinations thereof, such compound(s) in an amount at least partially sufficient to induce death of a cell of such a growth. In certain embodiments, $R_2$ can be selected from substituted and unsubstituted phenyl and substituted and unsubstituted thiophenyl; $R_1$ can be selected from H, alkyl, aminoalkyl, morpholinoalkyl, and hemisuccinate; Y can be selected from carbonyl, dimethylmethylene and hydroxymethylene; and Z can be selected from substituted and unsubstituted alkyl, phenyl, substituted phenyl, cycloalkyl, substituted cycloalkyl, thiophenyl and substituted thiophenyl. In yet other embodiments, Z can be an alkyl, phenyl, thiophenyl or a cycloalkyl moiety and, optionally, Y can be a dimethylmethylene or carbonyl moiety.

DETAILED DESCRIPTION OF CERTAIN EMBODIMENTS

Figure 1:
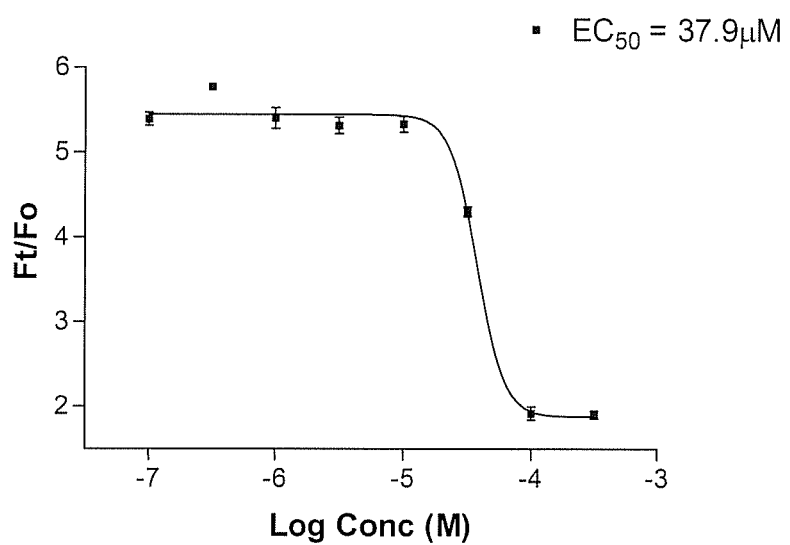
FIG. 1 shows the functional assay on compound 4c for the cannabinoid receptor 1.

The novel compounds encompassed by the instant invention are those described by the general Formula I set forth above, and the pharmaceutically acceptable salts and prodrugs thereof.

By "alkyl" in the present invention is meant straight or branched chain alkyl radicals having from 1-20 carbon atoms. Optionally, an alkyl group of the instant invention can contain one or more double bonds and/or one or more triple bonds, and thus can be specifically referred to as "alkenyl" or "alkynyl", respectively. Examples include but are not limited to methyl, ethyl, propyl, propenyl, propynyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as, for example, a halo, cycloalkyl, aryl, alkenyl, hydroxy or alkoxy group and the like.

By "cycloalkyl" is meant a carbocyclic radical having from three to twelve carbon atoms. The cycloalkyl can be monocyclic or a polycyclic fused system. Optionally, a cycloalkyl group of the instant invention can contain one or more double bonds and/or one or more triple bonds. Each cycloalkyl group may be optionally substituted with one, two or three substituents such as, for example, a halo, aryl, alkyl, hydroxy or alkoxy group and the like.

The term "heterocyclyl" refers to one or more carbocyclic ring systems of 4-, 5-, 6- or 7-membered rings which includes fused ring systems and contains at least one and up to four heteroatoms selected from nitrogen, oxygen or sulfur and combinations thereof. Each heterocyclyl group may be optionally substituted with one, two or three substituents such as, for example, a halo, aryl, alkyl, hydroxy or alkoxy group and the like.

By "aryl" is meant an aromatic carbocyclic radical having a single ring (e.g. phenyl), multiple rings (e.g. biphenyl) or multiple fused rings in which at least one is aromatic (e.g. 1,2,3,4-tetrahydronaphthyl). The aryl group can also be optionally mono-, di-, or trisubstituted with, for example, halo, alkyl, alkenyl, cycloalkyl, hydroxy or alkoxy and the like.

The term "heteroaryl" refers to one or multiple fused aromatic ring systems of from 5- to 12-membered rings containing at least one and up to four heteroatoms selected from nitrogen, oxygen or sulfur. Examples include but are not limited to furanyl, thienyl, pyridinyl, pyrimidinyl, benzimidazolyl and benzoxazolyl. The heteroaryl group can also be optionally mono-, di-, or trisubstituted with, for example, halo, alkyl, alkenyl, cycloalkyl, hydroxy or alkoxy and the like.

By "arylalkyl" is meant an alkyl radical substituted with an aryl, wherein the point of attachment of the arylalkyl to another moiety is a carbon of the alkyl chain.

As used herein, "substituted" refers to those substituents as would be understood by those skilled in the art. At least one and as many as five substituents can exist on a single group, unless otherwise stated exactly. Examples of such substituents include, but are not limited to, halo, alkyl, alkoxy, hydroxyl, aryl, heteroaryl, cycloalkyl, heterocycloalkyl, cyano, nitro, amino, alkylamino, dialkylamino, thiol, alkylthiol, haloalkyl (e.g. trifluoromethyl), carboxy, alkylcarboxy, carbamoyl and the like.

According to one approach, pyridine analogs can be prepared by reacting an intermediate pyridine 1 with the appropriate substituted 1-chloro-1-nitropropene according to the method of DiMauro et al., *Bioorg. Med. Chem. Lett.,* 17, 2305-2309 (2007) shown in Scheme 1. The ring formations are accomplished under microwave conditions with the appropriately substituted pyridine and substituted 1-chloro-1-nitropropene.

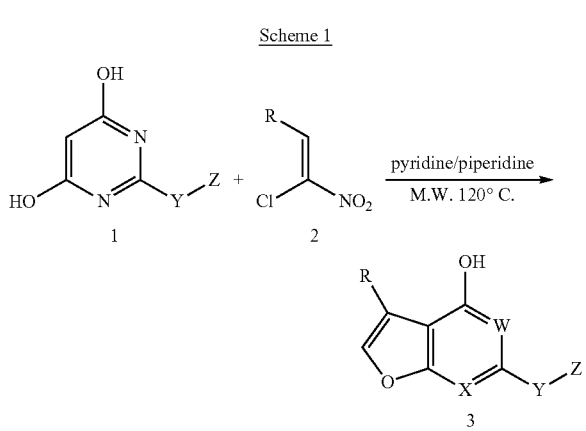

As shown in Scheme 2, the requisite pyridines are prepared by reacting dimethyl-, diethyl-, or bis(trichlorophenyl)-malonates with the appropriately substituted Schiff's base (See Ito and Miyajima, *J. Heterocycli Chem.,* 29:1037 (1992), and Kappe et al., *J. Heterocyclic Chem.,* 25:463 (1988)) derived from the requisite 2-keto analogs. In Scheme 2, $R_2$ is benzyl or t-butyl and $R_3$ and $R_4$ are methyl, ethyl, phenyl, bis(trichlorophenyl).

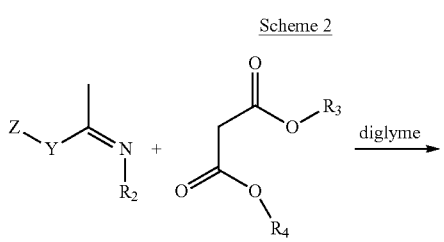

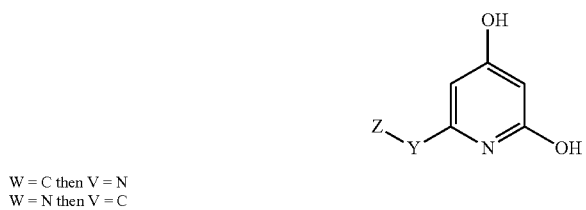

W = C then V = N
W = N then V = C

In turn, the substituted 2-keto compounds are either selected from commercially available compounds or synthesized from the appropriately substituted nitrile using methyl magnesium bromide or methyl lithium (Scheme 3). Alternatively, the nitrile can be reacted with methyl lithium to yield the required imine intermediate as shown in Scheme 4.

Scheme 3

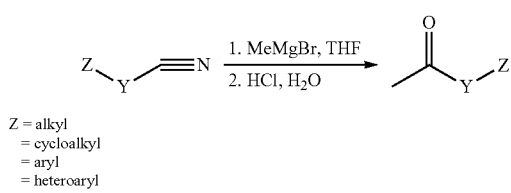

Z = alkyl
 = cycloalkyl
 = aryl
 = heteroaryl

Scheme 4

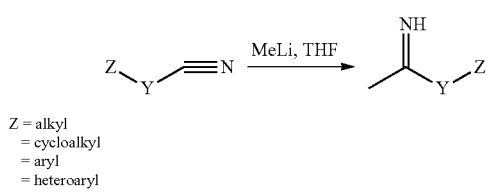

Z = alkyl
 = cycloalkyl
 = aryl
 = heteroaryl

The starting nitriles are derived from commercially available materials or synthesized using the methods shown in Schemes 5 and 6, which are representative of but not limited to the scope of the chemistry. Derivatives containing gem-dialkyl, heterocyclic, and carbocyclic substituent at Y, where commercial compounds are not available, are prepared either by direct alkylation of the methylene nitrile (Papahatjis et al., *J. Med. Chem.*, 50, 4048-4060 (2007)) or from the appropriately substituted aryl, heteroaryl halogen or isopropyl nitrile (Arseniyadis et al., "A review of the article Addn. and substitution reactions of nitrile-stabilized carbanions" Univ. Wyoming, Laramie, Wyo., USA; *Organic Reactions* (Hoboken, N.J., United States), 31 (1984)).

Scheme 5

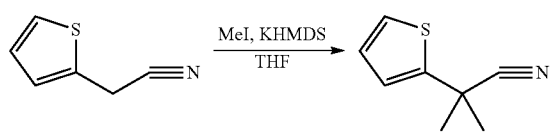

Scheme 6

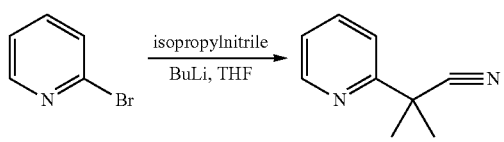

Derivatives containing a keto, hydroxyl or alkylhydroxyl substituent at Y can be prepared by direct oxidation of compounds bearing a Y=CH$_2$, or from the C2-aldehyde pyridine, prepared from 2,2-bis-ethylsulfanyl-acetaldehyde using previously reported chemistry (Bates et al., *Canadian Journal of Chemistry*, 61, 2006-9 (1983)) the resulting aldehyde is then transformed using previously reported chemistry (Moore et al., *Bioorg. & Med. Chem.*, 16:13, 6489-6500 2008)) (Scheme 7).

Scheme 7

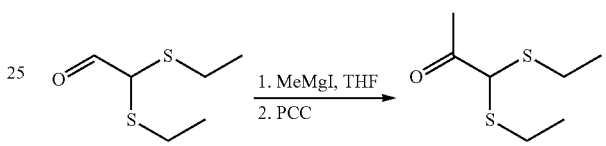

In certain embodiments, the compounds of formula I are where R$_2$ is selected from the group consisting of substituted or unsubstituted phenyl, and substituted or unsubstituted thiophen-2-yl; R$_1$ is selected from the group consisting of hydrogen, methyl and ethyl; Y is selected from the group consisting of C(O), CH$_2$, CH(CH$_3$), CH(OH), C(CH$_3$)(OH) and C(CH$_3$)$_2$; and Z is selected from the group consisting of substituted or unsubstituted phenyl, substituted or unsubstituted thiophen-2-yl, alkyl and substituted or unsubstituted cyclohexyl.

Likewise, the present invention contemplates, more broadly, various other such compounds, salts and/or prodrugs thereof, together with corresponding pharmaceutical compositions thereof, as also described in the aforementioned co-pending application. Such compounds, salts, prodrugs and/or pharmaceutical compositions can be used as described therein. For instance, the present invention can be used to modify the activity of one or more of the CB-1, CB-2, GPR-55, GPR-35, and GPR-119 receptors. Such a method can be carried out by contacting a cell and/or cannabinoid receptor thereof with a compound of the present invention, such contact at least partially sufficient to at least partially modify the activity of such a cannabinoid receptor, whether ex vivo or in vivo.

More generally, various physiological and/or therapeutic advantages of the present compounds and/or compositions can be realized with consideration of the authorities cited in the aforementioned co-pending application. The inventive analogs, as described herein, can be administered in therapeutically-effective amounts to treat a wide range of indications. Without limitation, various such conditions and/or disease states are described in paragraph 0067 of co-pending application Ser. No. 12/074,342 (the '342 application), filed Mar. 3, 2008 and entitled "Tri-Aryl/Heteroaromatic Cannabinoids and Use Thereof," the entirety of which is incorporated herein by reference. Examples include pain; peripheral pain; glaucoma; epilepsy; nausea such as associated with cancer chemotherapy; AIDS Wasting Syndrome; cancer (e.g., cutaneous T cell lymphoma, bronchopulmonary dysplasia, brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, etc.); neurodegenerative diseases (e.g., senile dementia, Multiple Sclerosis, Parkinson's Disease, Huntington's Chorea, and Alzheimer's Disease, etc.); to enhance appetite or otherwise treat or prevent food intake disorders (e.g., bulimia, anorexia, cachexia, obesity, type II diabetes mellitus (non-insulin dependent diabetes mellitus), etc.); schizophrenia; epilepsy; panic attacks; compulsive disorders; bipolar disorders; Raynaud's disease; thymus disorders; hypotension; insomnia; to reduce fertility; to prevent or reduce diseases associated with motor function such as Tourette's syndrome; to prevent or reduce inflammation in inflammatory diseases or conditions (e.g., renal ischemia, myocardial infarction, cerebral stroke, cerebral ischemia, nephritis, hepatitis, glomerulonephritis, cryptogenic fibrosing aveolitis, atopic dermatitis, vasculitis, scleroderma, etc.); to reduce the severity of immunomodulatory diseases or conditions (e.g., rheumatoid arthritis, systemic lupus erythematosus, retinal disease, osteoporosis, Paget's disease of bone, psoriasis, transplant rejection, allergy, seasonal allergic rhinitis, Crohn's disease, inflammatory bowel disease, etc.); to suppress memory; to produce peripheral vasodilation; and to treat respiratory diseases (e.g., sepsis, shock, sarcoidosis, idiopathic pulmonary fibrosis, reversible airway obstruction, adult respiratory distress syndrome, asthma, chronic obstructive pulmonary disease (COPD), bronchitis, etc.). See United States Patent Application Publication Nos. 20050137173 to Makriyannis, 20060100228 to Shankar et al., and 20070021398 to Torrens et al., each of which is hereby incorporated by reference in its entirety.

Accordingly, this invention can be directed to a method comprising providing a compound of the sort described herein, such a compound exhibiting activity at a cannabinoid receptor; and contacting a cell comprising a cannabinoid receptor with such a compound and/or administering such a compound to a patient, such a compound in an amount at least partially effective to treat a cannabinoid receptor/mediated condition. Such a cannabinoid receptor can be a receptor described herein or as would otherwise be understood or realized by those skilled in the art made aware of this invention.

The activity of cannabinoid and related receptors can be affected, mediated and/or modified by contacting such a receptor with an effective amount of one or more of the present compounds as can be present in or as part of a pharmaceutical composition or treatment, or by contacting a cell comprising such a receptor with an effective amount of one or more such compounds, so as to contact such a receptor in the cell therewith. Contacting may be in vitro or in vivo. Accordingly, as would be understood by those skilled in the art, "contact" means that a cannabinoid and/or related receptor and one or more compounds are brought together for such a compound to bind to or otherwise affect or modify receptor activity. Amounts of one or more such compounds effective to modify and/or affect receptor activity can be determined empirically and making such a determination is within the skill in the art.

Without limitation, analog compounds of this invention can be used ex vivo in receptor binding assays of the sort described in Example 2 of the aforementioned co-pending '342 application. In vitro activity of the present analog compounds can be demonstrated in a manner similar to that described in Example 3 of the co-pending application. Alternatively, in vivo activity can be demonstrated using the protocols described in Examples 4 and 6, thereof. More specifically, anti-cancer activity of various representative compounds of this invention can be shown against human lung, prostate, colorectal and pancreatic cancer cell lines using the methodologies described in Example 9 of the aforementioned co-pending '342 application. Extending such a methodology, the present invention can also be used to treat cancer growth of the central nervous system and/or induce cellular death within such growth. In accordance with this invention, various cannabinoid compounds of the sort described herein, including but not limited to those discussed above, can also be used in conjunction with a method to treat human glioma and/or brain cancers. Illustrating such embodiments, one or more compounds of the present invention can be provided and used, as described in the co-pending application, to contact and/or treat human brain cancers, such contact and/or treatment as can be confirmed by cell death and/or related effects.

In addition, the present invention also relates to the use of pro-drugs for the compounds of formula (I). A pro-drug is an inactive compound, which when administered is converted into an active form. See *Medicinal Chemistry Principles and Practice*, ISBN 0-85186-494-5, F. D. King (ed.), p. 215 (1994).

Exemplary pro-drugs include, without limitation, esters of the type described in U.S. Pat. No. 6,008,383 to Elsohly (describing esters of THC); and hydroxyl-derived groups or (primary or secondary) amine-derived groups as described in U.S. Pat. No. 7,109,216 to Kruse (heterocyclic cannabinoids amino or hydroxyl pro-drugs), each of which is hereby incorporated by reference in its entirety. The design and manufactured of these pro-drugs is fully described in the above-listed references. Preferred amino or hydroxyl-derived pro-drugs are those that include the following derivative groups: amidine, enamine, Mannich base, a hydroxyl-methylene derivative, an O-(acyloxymethylene carbamate) derivative, carbamate, ester, amide, and enaminone. The THC esters are particularly preferred, because they are believed to have excellent solubility profiles.

The compounds of the invention, as well as their salts and/or pro-drugs, are present in an amount effective to achieve the intended purpose of administration. While individual needs vary, determination of optimal ranges of effective amounts of each component is within the skill of the art. The quantity of such one or more compounds, salts and/or pro-drug administered will vary depending on the patient and the mode of administration and can be any effective amount. Typical dosages include about 0.01 to about 100 mg/kg·body wt, more preferably between about 0.01 to about 1.0 mg/kg·body wt up to three times a day. Treatment regimen for the administration of the compounds of the present invention can also be determined readily by those with ordinary skill in art. The quantity of the compound administered may vary over a wide range to provide in a unit dosage an effective amount of from about 0.01 to 20 mg/kg of body weight of the patient per day to achieve the desired effect. Single doses are preferably between about 1 mg and about 1000 mg/per dose.

A pharmaceutically acceptable carrier comprise any suitable adjuvant, carrier, excipient, stabilizer, or combination thereof, and the pharmaceutical composition can be in solid or liquid form such as, tablets, capsules, powders, solutions, suspensions, or emulsions. Typically, the composition will contain from about 0.01 to about 99 percent, preferably from about 20 to about 75 percent of active compound(s), salt, or pro-drug, together with the adjuvants, carriers and/or excipients.

For oral therapeutic administration, the active compounds, salt, or pro-drug can be incorporated with excipients and used in the form of tablets, capsules, elixirs, suspensions, syrups, and the like.

The solid unit dosage forms (e.g., tablet or capsule) can be of the conventional type. For example, the compounds can be combined with one or more lubricants and/or inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

Oral liquid dosages can contain aqueous or alcohol-based carriers, along with sweeteners, such as corn syrup, saccharine, aspartame, etc., natural or artificial flavoring agents, and optionally one or more dyes.

Forms suitable for injectable use include colloidal dispersions, microemulsions, and sterile powders for the extemporaneous preparation of sterile injectable dispersions or microemulsions. In all cases, the form should be sterile and should be fluid to the extent that easy syringability exists. It should be stable under the conditions of manufacture and storage and should be preserved against the contaminating action of microorganisms, such as bacteria and fungi. The solutions or suspensions of the active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol can be utilized in combination with the microemulsions, as preformulations. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Transdermal delivery devices can also be used, such as the transdermal delivery described in U.S. Patent Application Publ. No. 20060257463 to Elsohly.

Depending upon the treatment being effected, the compounds or compositions of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

EXAMPLES OF THE INVENTION

The following non-limiting examples and data illustrate various aspects and features relating to the compounds, compositions and/or methods of the present invention, including the synthesis of furanopyridine cannabinoid receptor ligands and/or compounds, as are available though the methodologies described herein. In comparison with the prior art, the present compounds and methods provide results and data which are surprising, unexpected and contrary thereto. While the utility of this invention is illustrated through the preparation and use of several compounds, moieties and/or substituents thereof, it will be understood by those skilled in the art that comparable results are obtainable with various other compounds, moieties and/or substituents, as are commensurate with the scope of this invention.

The disclosures in this application of all articles and references, including patents, are incorporated herein by reference. All compounds are named using ChemBioDraw Ultra Version 11.0.01 or 12.0.

Example 1

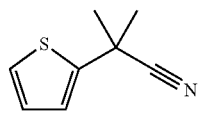

1a

2-Methyl-2-(thiophen-2-yl)propanenitrile

To a solution of 2-(thiophen-2-yl)acetonitrile (1 g, 8.13 mmol) in 4 ml anhydrous THF, KHMDS (24.4 mmol, 48.9 ml, 0.5 M in toluene) is added at 0° C. The mixture is allowed to stir for 3 minutes, after which a solution of 16.26 mmol iodomethane (1.13 ml in 26 ml anhydrous THF) is added slowly over a period of 10 minutes. The mixture is stirred for another 5 minutes and monitored by TLC. Upon completion, the reaction is quenched with aqueous ammonium chloride. The organic phase is separated with ethyl acetate and dried over sodium sulfate. The product is purified via vacuum distillation (bp 42° C. at 1 torr). Yield 89%; $^1$H NMR (500 MHz, CDCl$_3$): δ (ppm) 7.4 (d, 1H), 7.2 (t, 1H), 7.0 (d, 1H), 1.9 (s, 6H).

In a similar fashion the following compounds are synthesized.

1b 2,2-Dimethyloctanenitrile

Purified via vacuum distillation (bp 50-55° C. at 1.1 ton). Yield 84%; I.R. (neat) nitrile 2230 cm$^{-1}$; $^1$H NMR (500 MHz, CDCl$_3$): δ (ppm) 1.5 (m, 4H). 1.4-1.3 (m, 12H), 0.9 (s, 3H).

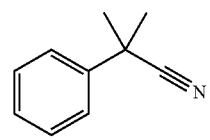

1c

2-Methyl-2-phenylpropionitrile

To a solution of fluorobenzene (5.85 mL, 62.4 mmol) in 100 mL of anhydrous toluene is added isobutyronitrile (22.5 mL, 250 mmol) followed by 200 mL (100 mmol) of a 0.5 M solution of KHMDS in toluene. The reaction is then stirred at 80° C. for 24 hours. The reaction is then allowed to cool to room temperature, diluted with diethyl ether, and washed with water and brine. The organic fraction is then dried over sodium sulfate and concentrated under reduced pressure. The product is purified by flash chromatography using an ethyl acetate/hexanes gradient to yield 4.57 g (50% yield) of the objective compound as a brown oil. MS: (ESI, Pos) m/z 168.0 (M+23); $^1$H NMR (500 MHz, CDCl$_3$): δ (ppm) 7.48 (d, 2H), 7.39 (t, 2H), 7.31 (t, 1H), 1.73 (s, 6H).

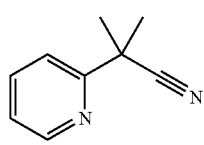

1d

2-Methyl-(2-pyridin-2-yl)propionitrile

Purified in a manner similar to 1c using 2-bromopyridine as the starting material to yield a brown oil. MS: (ESI, Pos) m/z 168.9 (M+23).

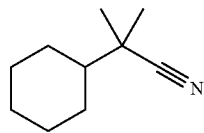

1e

2-Cyclohexyl-2-methylpropionitrile $^1$H NMR (500 MHz, CDCl$_3$): δ (ppm) 1.88 (m, 1H), 1.83 (m, 2H), 1.68 (t, 2H), 1.61 (m, 2H), 1.40-1.08 (m, 6H), 1.12 (s, 6H).

Example 2

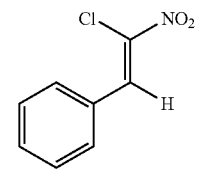

2a (2-Chloro-2-nitrovinyl)benzene

Benzaldehyde (3.59 g, 33.8 mmol), bromonitromethane (9.0 g, 64.3 mmol), dimethylamine hydrochloride (24.8 g, 304.2 mmol), potassium fluoride (0.3 g, 5.08 mmol) and m-xylenes (50 mL) are combined in a 250 mL round bottomed flask and connected to a Dean-Stark trap. The mixture is heated at 125° C. with azeotropic removal of water for 8 hours. The solvent is removed under reduced pressure and the residue is extracted with a mixture of 1:1 dichloromethane and water. After separation of organic layer, the aqueous layer is extracted three times with dichloromethane. The combined organics are dried over anhydrous Na$_2$SO$_4$ and concentrated to afford a brown oil. The oily residue is purified on a silica column (biotage system) using 10% ethyl acetate/hexane mixture to produce clean product in the form of pale yellow needles (4.8 mg, 77%). Rf (10% ethyl acetate/hexane): 0.66; $^1$H NMR (300 MHz, CDCl$_3$): δ 8.40 (s, 1H), 7.86-7.90 (m, 2H), 7.51-7.5 (m, 3H).

The following compounds are prepared in a similar manner

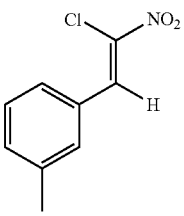

2b (2-Chloro-2-nitrovinyl)-3-methylbenzene $^1$H NMR (300 MHz, CDCl$_3$): δ 8.38 (s, 1H), 7.67 (t, 2H), 7.36-7.41 (m, 2H), 2.45 (s, 3H).

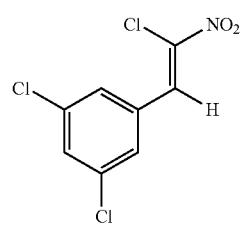

2c 1,3-Dicloro-5-(2-chloro-2-nitrovinyl)benzene $^1$H NMR (300 MHz, CDCl$_3$): δ 8.23 (s, 1H), 7.74 (d, 2H), 7.52 (s, 1H).

2d 2-(2-Chloro-2-nitrovinyl)thiophene $^1$H NMR (300 MHz, CDCl$_3$): δ 8.65 (s, 1H), 7.81 (d, J=5.1 Hz, 1H), 7.69 (d, 1H), 7.27-7.28 (t, 1H).

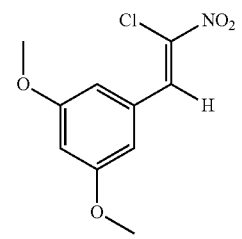

2e 1-(2-Chloro-2-nitrovinyl)-3,5-dimethoxybenzene

¹H NMR (500 MHz, CDCl₃): ∂ 8.30 (s, 1H), 6.98 (d, 2H), 6.62 (s, 1H), 3.84 (s, 6H).

Example 3

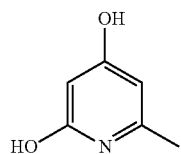

3a

6-Methylpyridine-2,4-diol

A solution of acetone (1 g, 17.2 mmol) and benzylamine (1.7 g, 16.3 mmol) in benzene (40 mL) is added to 4 g of powdered molecular sieves and the reaction is stirred at room temperature overnight. The sieves are filtered, the solvent removed under reduced pressure and the resulting residue is purified by column chromatography.

The following compounds are prepared in a similar manner.

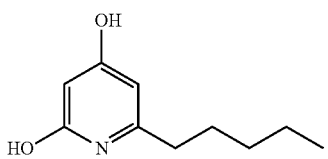

3b

6-Pentylpyridine-2,4-diol

Into a round bottomed flask fitted with a Dean-Stark trap and condenser is added a solution of 2-heptanone (1 g, 8.7 mmol) and benzylamine (0.9 g, 8.3 mmol) in benzene (40 ml). The mixture is refluxed overnight yielding approximately 0.1 mL of water in the trap (64% yield of the enamine based on collected water). The solvent is removed and the enamine purified by column chromatograph.

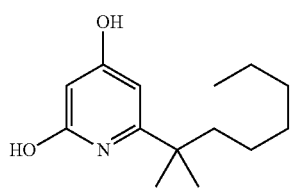

3c 6-(2-Methyloctan-2-yl)pyridine-2,4-diol

White powder, yield: 40%; MS: (ESI, Neg) 235.8 (M−1); ¹HNMR (300 MHz, DMSO-d6): ∂(ppm) 10.78 (s, 1H), 10.3 (s, 1H), 5.36 (s, 1H), 5.35 (s, 1H), 1.59 (t, 2H), 1.33 (s, 6H), 1.28 (m, 8H), 0.83 (t, 3H).

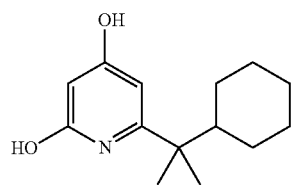

3d 6-(2-Cyclohexylpropan-2-yl)pyridine-2,4-diol

Off white powder, yield: 35%; MS: (ESI, Neg) 227.8 (M−1); ¹HNMR (300 MHz, DMSO-d6): ∂(ppm) 10.55 (s, 5.60 (s, 1H), 5.36 (s, 1H), 1.76 (m, 1H), 1.67 (m, 6H), 1.39 (m, 8H), 1.17 (m, 2H).

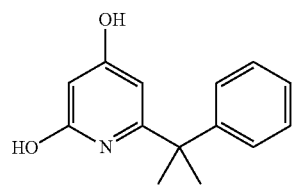

3e 6-(2-Phenylpropan-2-yl)pyridine-2,4-diol

Off white powder, yield: 39%; MS: (ESI, Neg) 227.8 (M−1); ¹HNMR (300 MHz, DMSO-d6): ∂(ppm) 10.32 (s, 1H), 7.33 (m, 5H), 5.71 (s, 1H), 5.35 (s, 1H), 1.57 (s, 6H).

Example 4

The target compounds are prepared as described above in Scheme 1.

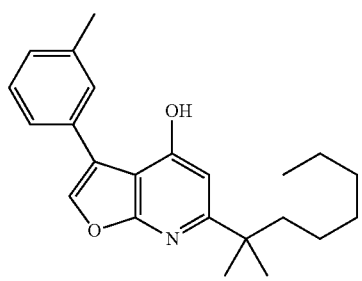

4a 6-(2-Methyloctan-2-yl)-3-m-tolylfuro[2,3-b]pyridin-4-ol (4a)

White powder, yield: 27%; MS: (ESI, Pos) 374.3 (M+1); ¹HNMR (300 MHz, CDCl₃): ∂(ppm) 9.10 (s, 1H), 7.61 (m, 3H), 7.28 (m, 1H), 7.21 (m, 1H), 6.40 (s, 1H), 2.43 (s, 3H), 1.58 (s, 2H), 1.33 (s, 6H), 1.21 (m, 8H), 0.85 (t, 3H).

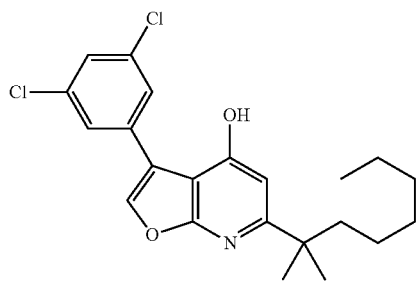

3-(3,5-Dichlorophenyl)-6-(2-methyloctan-2-yl)furo[2,3-b]pyridin-4-ol (4b)

White powder, yield: 30%; MS: (ESI, Pos) 428.2 (M+1); $^1$HNMR (300 MHz, CDCl$_3$): ∂(ppm) 10.6 (s, 1H), 7.85 (d, 2H), 7.64 (s, 1H), 7.35 (m, 1H), 6.42 (s, 1H), 1.59 (m, 2H), 1.33 (s, 6H), 1.12 (m, 8H), 0.79 (t, 3H).

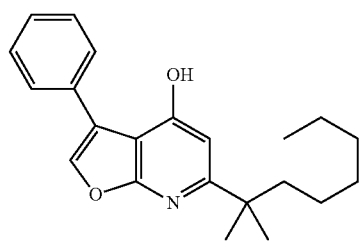

6-(2-Methyloctan-2-yl)-3-phenylfuro[2,3-b]pyridin-4-ol (4c)

White needles, yield: 35% MS: (ESI, Pos) 360.6 (M+1); $^1$HNMR (500 MHz, DMSO-d$_6$): ∂(ppm) 11.34 (s, 1H), 7.95 (d, 2H), 7.61 (s, 1H), 7.39 (m, 3H), 6.34 (s, 1H), 1.67 (m, 2H), 1.33 (s, 6H), 1.15 (m, 8H), 0.76 (t, 3H).

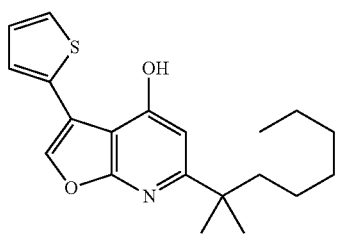

6-(2-Methyloctan-2-yl)-3-(thiophen-2-yl)furo[2,3-b]pyridin-4-ol (4d)

White needles, yield: 35%; MS: (ESI, Pos) 360.6 (M+1); $^1$HNMR (500 MHz, DMSO-d$_6$): ∂(ppm) 11.34 (s, 1H), 7.95 (d, 2H), 7.61 (s, 1H), 7.39 (m, 3H), 6.34 (s, 1H), 1.67 (m, 2H), 1.33 (s, 6H), 1.15 (m, 8H), 0.76 (t, 3H).

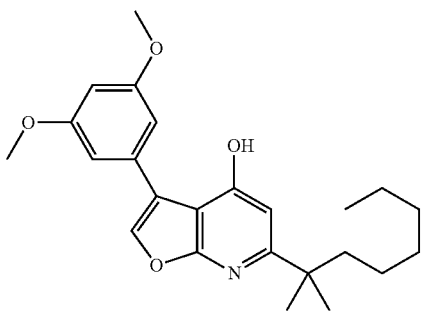

3-(3,5-Dimethoxyphenyl)-6-(2-methyloctan-2-yl)furo[2,3-b]pyridin-4-ol (4e)

White powder, yield: 32%; MS: (ESI, Pos) 420.3 (M+1) $^1$HNMR; (300 MHz, CDCl$_3$): ∂(ppm) 9.83 (s, 1H), 7.65 (s, 1H), 7.16 (m, 2H), 6.48 (m, 1H), 6.40 (s, 1H), 3.86 (s, 6H), 1.55 (m, 2H), 1.31 (s, 6H), 1.16 (m, 8H), 0.82 (t, 3H).

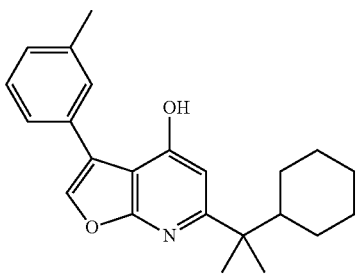

6-(2-Cyclohexylpropan-2-yl)-3-m-tolylfuro[2,3-b]pyridin-4-ol (4f)

MS: (ESI, Neg) m/z 348.0 (M−1).

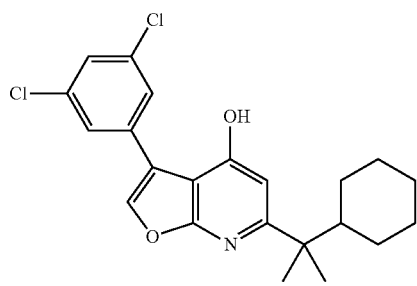

6-(2-Cyclohexylpropan-2-yl)-3-(3,5-dichlorophenyl)furo[2,3-b]pyridin-4-ol (4g)

Yield: 12.4%; MS: (ESI, Neg) m/z 402.2 (M−1); $^1$H NMR (500 MHz, CDCl$_3$): δ 10.70 (s, 1H), 7.85 (s, 2H), 7.64 (s, 1H), 7.32 (s, 1H), 6.41 (s, 1H), 1.55 (m, 6H), 1.24 (s, 6H), 1.16 (m, 3H), 0.89 (m, 2H).

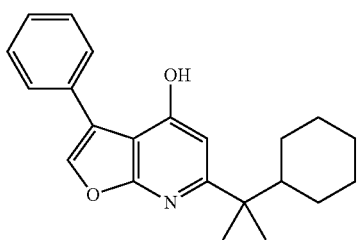

6-(2-Cyclohexylpropan-2-yl)-3-phenylfuro[2,3-b]pyridin-4-ol (4h)

MS: (ESI, Neg) m/z 334.0 (M−1).

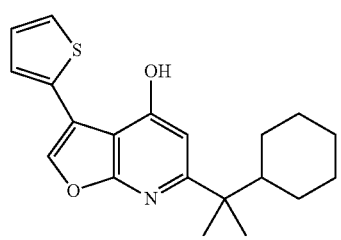

6-(2-Cyclohexylpropan-2-yl)-3-(thiophen-2-yl)furo[2,3-b]pyridin-4-ol (4i)

Yield: 8.3%; MS: (ESI, Neg) m/z 340.0 (M−1); $^1$H NMR (500 MHz, CDCl$_3$): δ 10.06 (s, 1H), 8.10 (d, 1H), 7.69 (s, 1H), 7.23 (d, 1H), 7.08 (t, 1H), 6.39 (s, 1H), 1.60 (m, 4H), 1.49 (d, 2H), 1.29 (s, 6H), 1.06 (m, 3H), 0.95 (m, 2H).

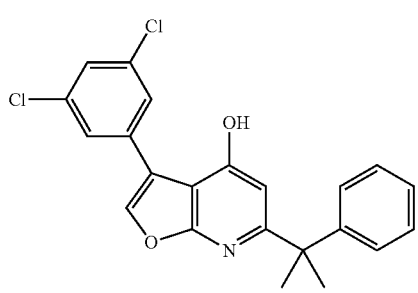

5-(3,5-Dichlorophenyl)-2-(2-(thiophen-2-yl)propan-2-yl)furo[2,3-a]pyrimidin-4-ol (4j)

Yield: 14.3%; MS: (ESI, Pos) m/z 420.0 (M+23); $^1$H NMR (500 MHz, CDCl$_3$): δ 8.12 (s, 1H), 7.61 (d, 2H), 7.47 (m, 1H), 7.36 (m, 2H), 7.28 (m, 3H), 6.13 (s, 1H), 1.65 (s, 6H).

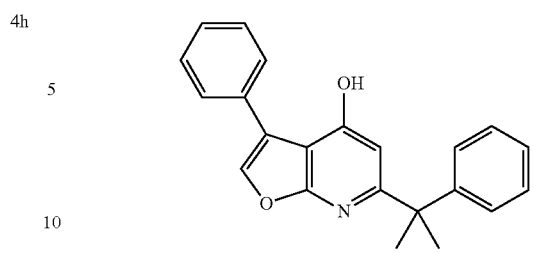

3-Phenyl-6-(2-phenylpropan-2-yl)furo[2,3-b]pyridin-4-ol (4k)

Yield: 9.7%; MS: (ESI, Pos) m/z 352.1 (M+23); $^1$H NMR (500 MHz, CDCl$_3$): δ 7.93 (m, 2H), 7.84 (t, 2H) 7.62 (m, 3H), 7.55 (s, 1H), 7.47 (m, 3H), 6.15 (s, 1H), 1.68 (s, 6H).

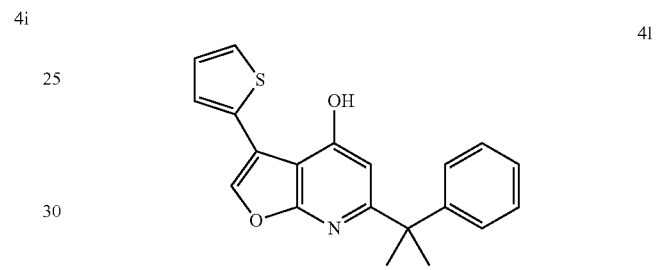

6-(2-Phenylpropan-2-yl)-3-(thiophen-2-yl)furo[2,3-b]pyridin-4-ol (4l)

Yield: 9.6%; MS: (ESI, Pos) m/z 358.1 (M+23); $^1$H NMR (500 MHz, CDCl$_3$): δ 7.99 (d, 1H), 7.72 (s, 1H), 7.33 (t, 2H), 7.27 (m, 3H), 7.23 (d, 1H), 7.07 (t, 1H), 6.61 (s, 1H), 1.70 (s, 6H).

Example 7

Receptor Binding Assays

Cell membranes from HEK293 cells transfected with the human CB-1 receptor and membranes from CHO-K1 cells transfected with the human CB-2 receptor are prepared. [$^3$H] CP 55,940 having a specific activity of 120 Ci/mmol is obtained from Perkin-Elmer Life Sciences, Inc. All other chemicals and reagents are obtained from Sigma-Aldrich. The assays are carried out in 96 well plates obtained from Millipore, Inc. fitted with glass fiber filters (hydrophilic, GFC filters) having a pore size of 1.2μ. The filters are soaked with 0.05% polyethyleneimine solution and washed 5× with deionized water prior to carrying out the assays. The filtrations are carried out on a 96 well vacuum manifold (Millipore Inc.), the filters punched out with a pipette tip directly into scintillation vials at the end of the experiment, and the vials filled with 5 ml scintillation cocktail Ecolite (+) (Fisher Scientific). Counting is carried out on a Beckmann Scintillation Counter model LS6500. Drug solutions are prepared in DMSO and the radioligand is dissolved in ethanol.

Incubation buffer: 50 mM TRIS-HCl, 5 mM $MgCl_2$, 2.5 mM EDTA, 0.5 mg/ml fatty acid free bovine serum albumin, pH 7.4.

Binding protocol for the CB-1 receptor: 8 μg of membranes (20 μl of a 1:8 dilution in incubation buffer) is incubated with 5 μl of drug solution ($10^{-4}$M to $10^{-12}$M) and 5 μl of 5.4 nM [$^3$H]CP 55,940 in a total volume of 200 μl for 90 mins at 30° C. Non-specific binding is determined using 10 μM WIN55, 212-2 ($K_i$=4.4 nM). The membranes are filtered and the filters washed 7× with 0.2 ml ice-cold incubation buffer and allowed to air dry under vacuum.

Binding protocol for the CB-2 receptor: 15.3 μg of membranes (20 μl of a 1:20 dilution in incubation buffer) is incubated with 5 μl of drug solution ($10^{-4}$M to $10^{-12}$M) and 5 μl of 10 nM [$^3$H]CP 55,940 in a total volume of 200 μl for 90 minutes at 30° C. Non-specific binding is determined using 10 μM WIN55, 212-2 ($K_i$=4.4 nM). The membranes are filtered and the filters washed 7× with 0.2 ml ice-cold incubation buffer and allowed to air dry under vacuum.

Data accumulation and statistical analysis: Varying concentrations of drug ranging from $10^{-4}$M to $10^{-12}$M are added in triplicate for each experiment and the individual molar $IC_{50}$ values are determined using GraphPad Prism. The corresponding $K_i$ values for each drug are determined utilizing the Cheng and Prusoff equation and final data is presented as $K_i$±S.E.M. of n≧2 experiments.

Functional assays: HEK-293 cell lines stably transfected with a cyclic nucleotide-gated channel and either human CB-1 or CB-2 receptors (BD Biosciences, San Jose, Calif. USA) are seeded in poly-D-lysine coated 96-well plates at a density of 70,000 cells per well. Plates are incubated at 37° C. in 5% $CO_2$ overnight prior to assay. Plates are then removed from the incubator and the complete growth medium (DMEM, 10% FBS, 250 μg/ml G418 and 1 μg/ml puromycin) is replaced with 1004, DMEM containing 0.25% BSA. Next, 1004 membrane potential dye loading buffer (Molecular Devices, Sunnyvale, Calif. USA) is prepared according to the manufacturer. The plates are placed back into the incubator for 30 minutes and then the baseline fluorescence is read on a BioTek Synergy 2 multi-mode microplate reader (BioTek Instruments, Winooski, Vt. USA) with 540 nm excitation and 590 nm emission filters prior to drug addition. Drugs are added in 50 μL DPBS containing 2.5% DMSO, 1.25 μM 5'-(N-ethylcarboxamido) adenosine and 125 μM Ro 20-1724. Plates are then incubated at room temperature for 25 minutes and fluorescence measured again at 540 nm excitation and 590 nm emission.

Figure 2:
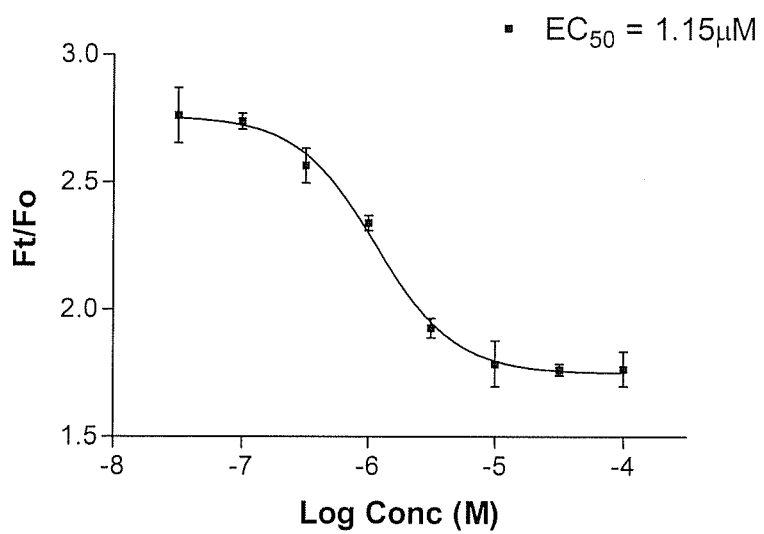
FIG. 2 shows the functional assay on compound 4c for the cannabinoid receptor 2.
Figure 3:
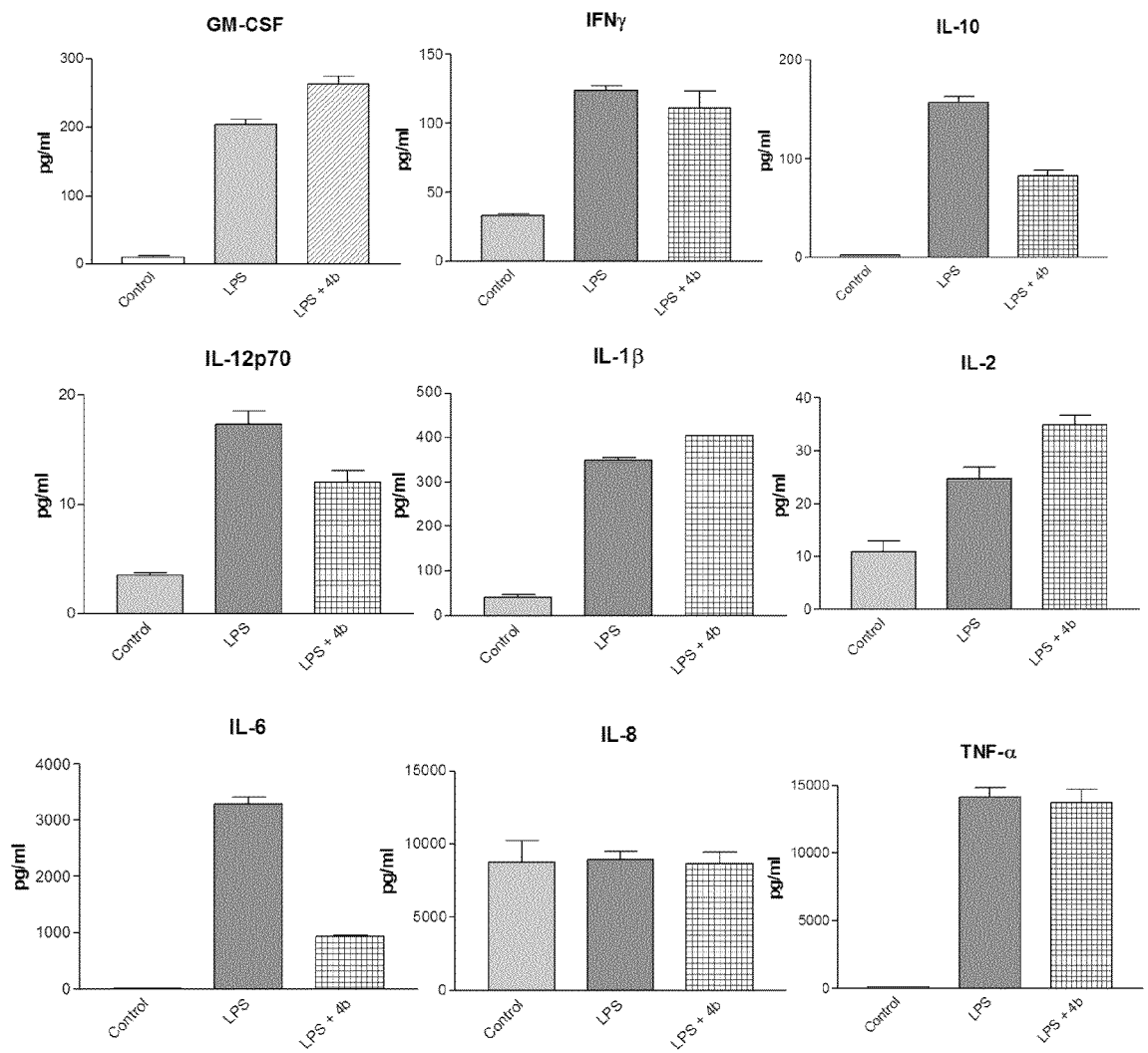
FIG. 3 shows the anti-inflammatory activity of compound 4b as determined by cytokine release profiles in THP-1 cells stimulated with LPS.
Figure 4:
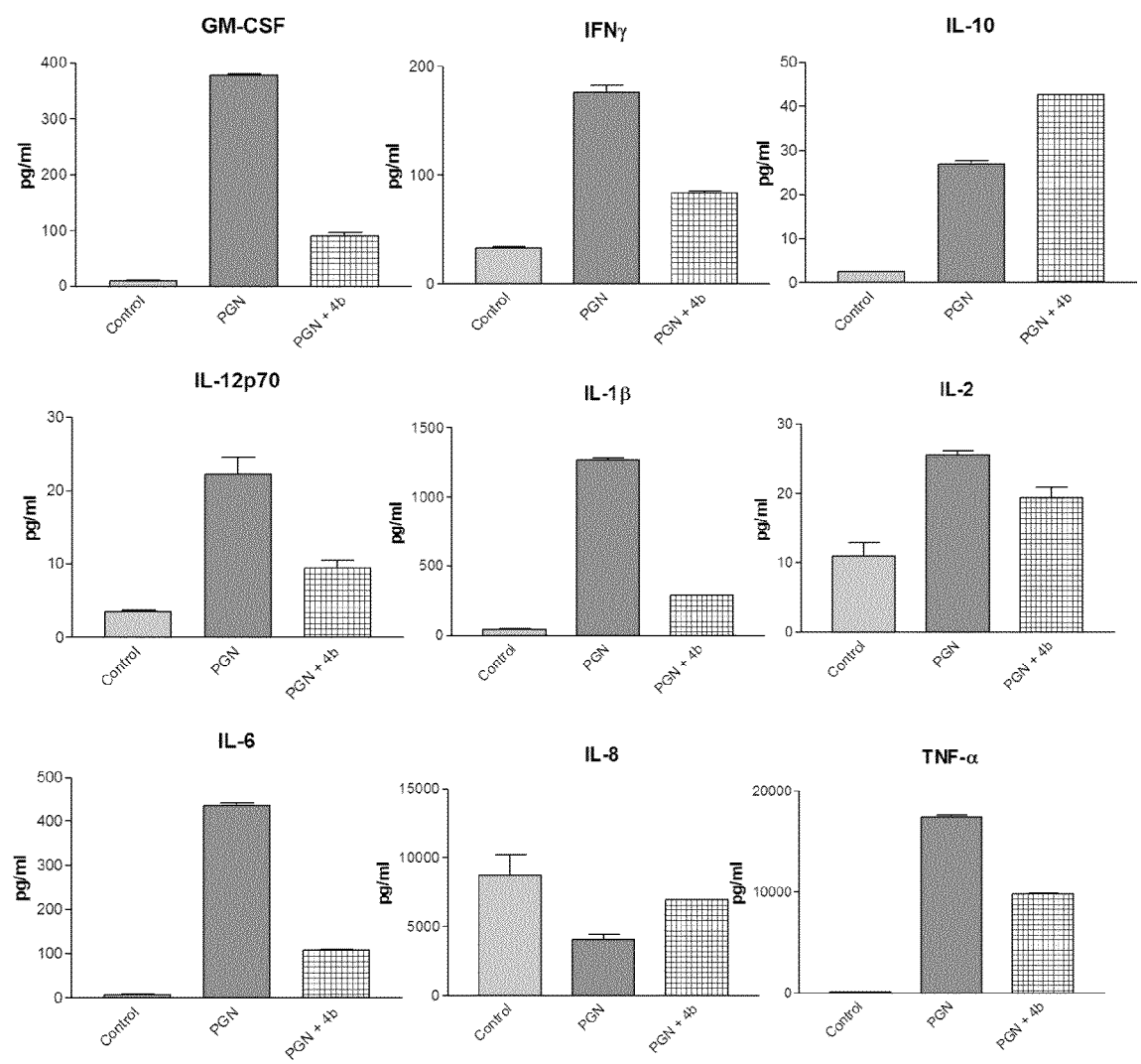
FIG. 4 shows the anti-inflammatory activity of compound 4b as determined by cytokine release profiles in THP-1 cells stimulated with PGN.
Figure 5:
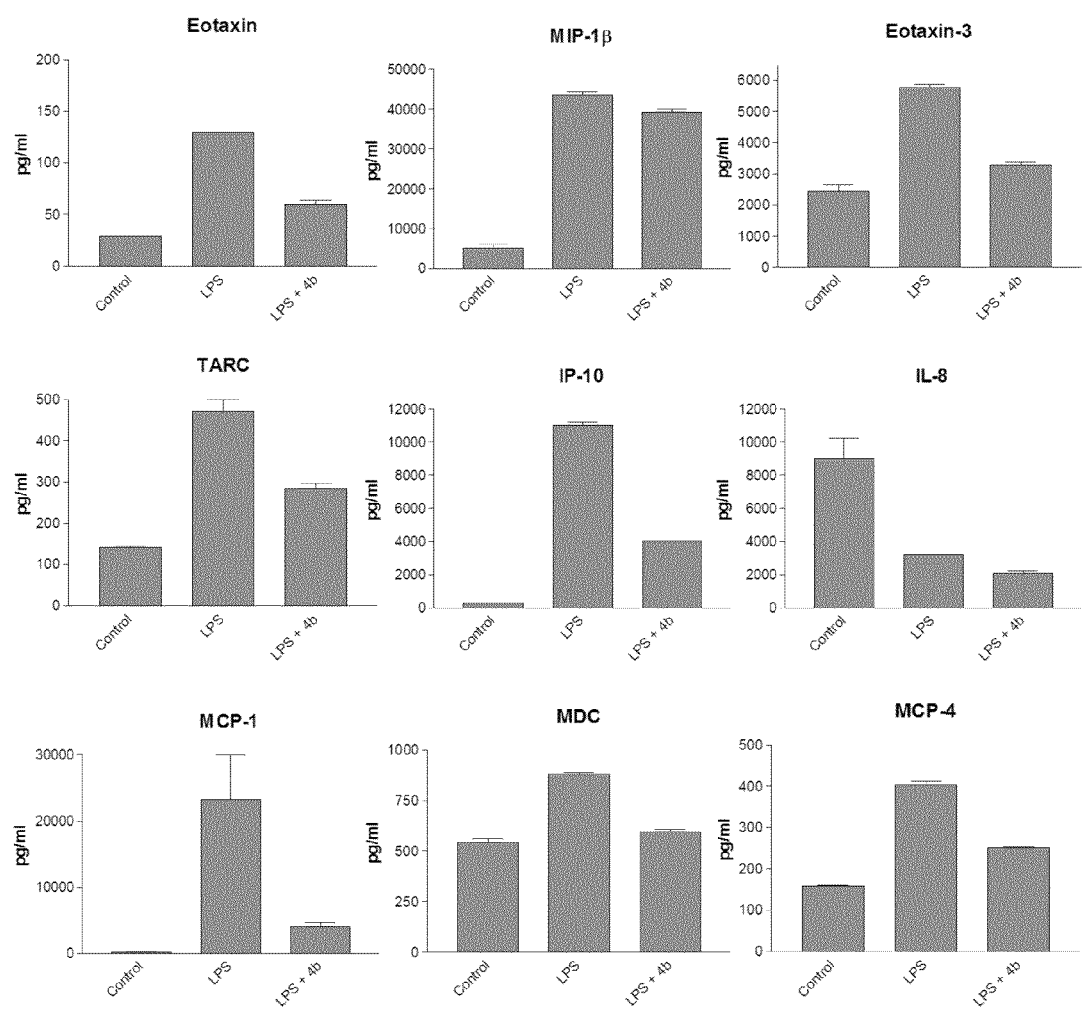
FIG. 5 shows the anti-inflammatory activity of compound 4b as determined by chemokine release profiles in THP-1 cells stimulated with LPS.
Figure 6:
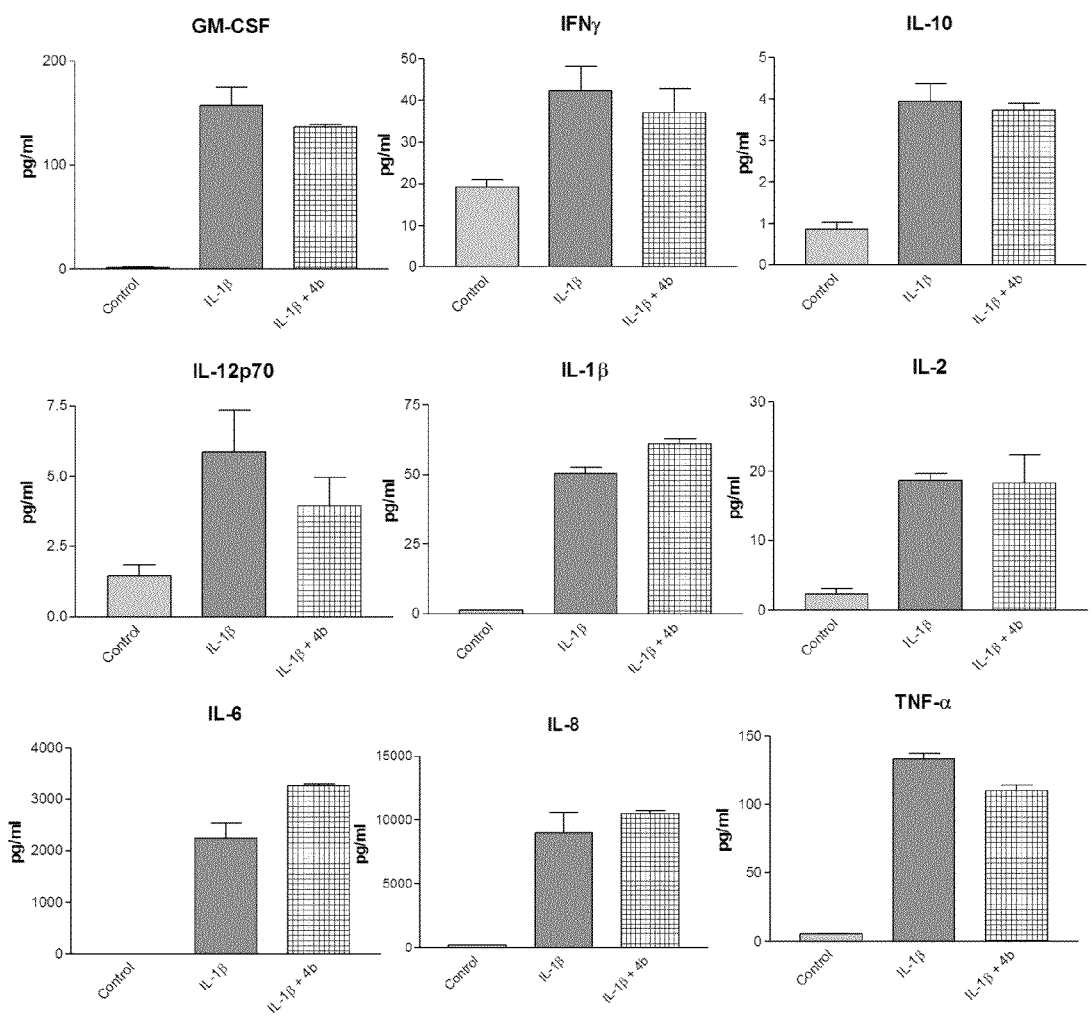
FIG. 6 shows the anti-inflammatory activity of compound 4b as determined by cytokine release profiles in A549 cells stimulated with IL-1β.
Figure 7:
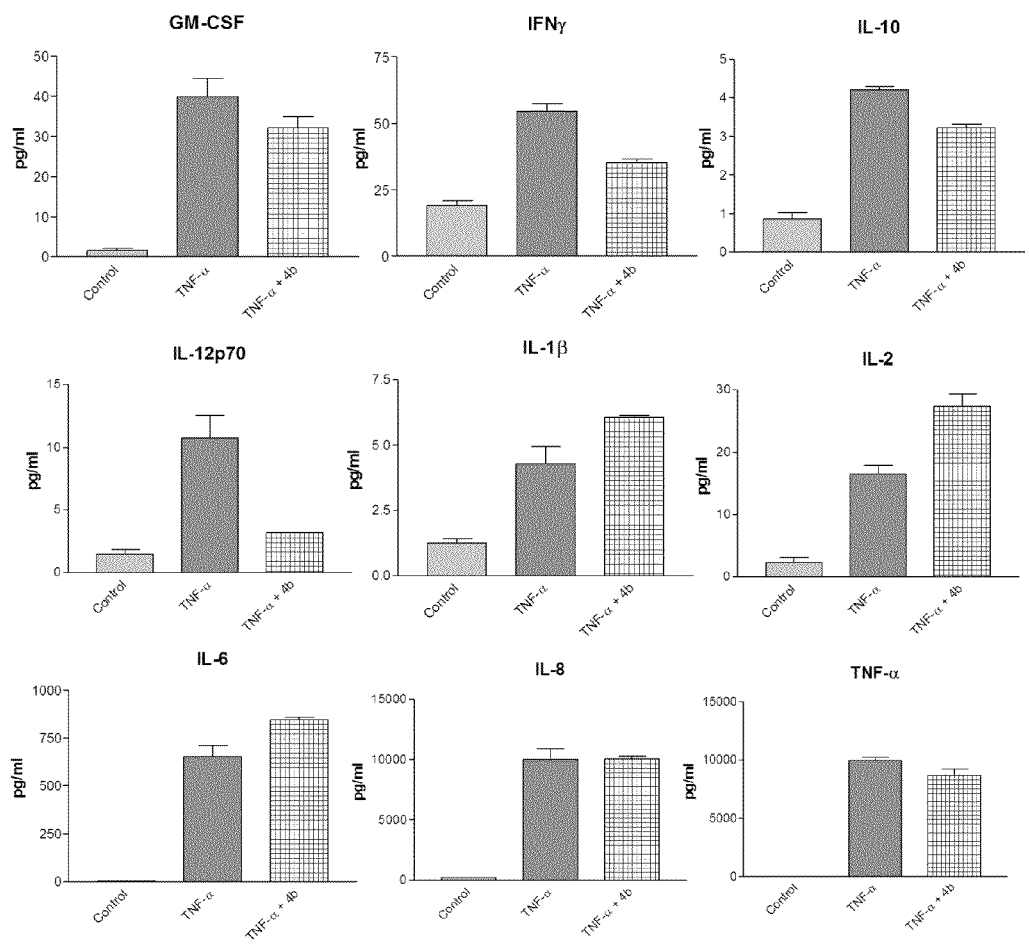
FIG. 7 shows the anti-inflammatory activity of compound 4b as determined by cytokine release profiles in A549 cells stimulated with TNF-α.
Figure 8:
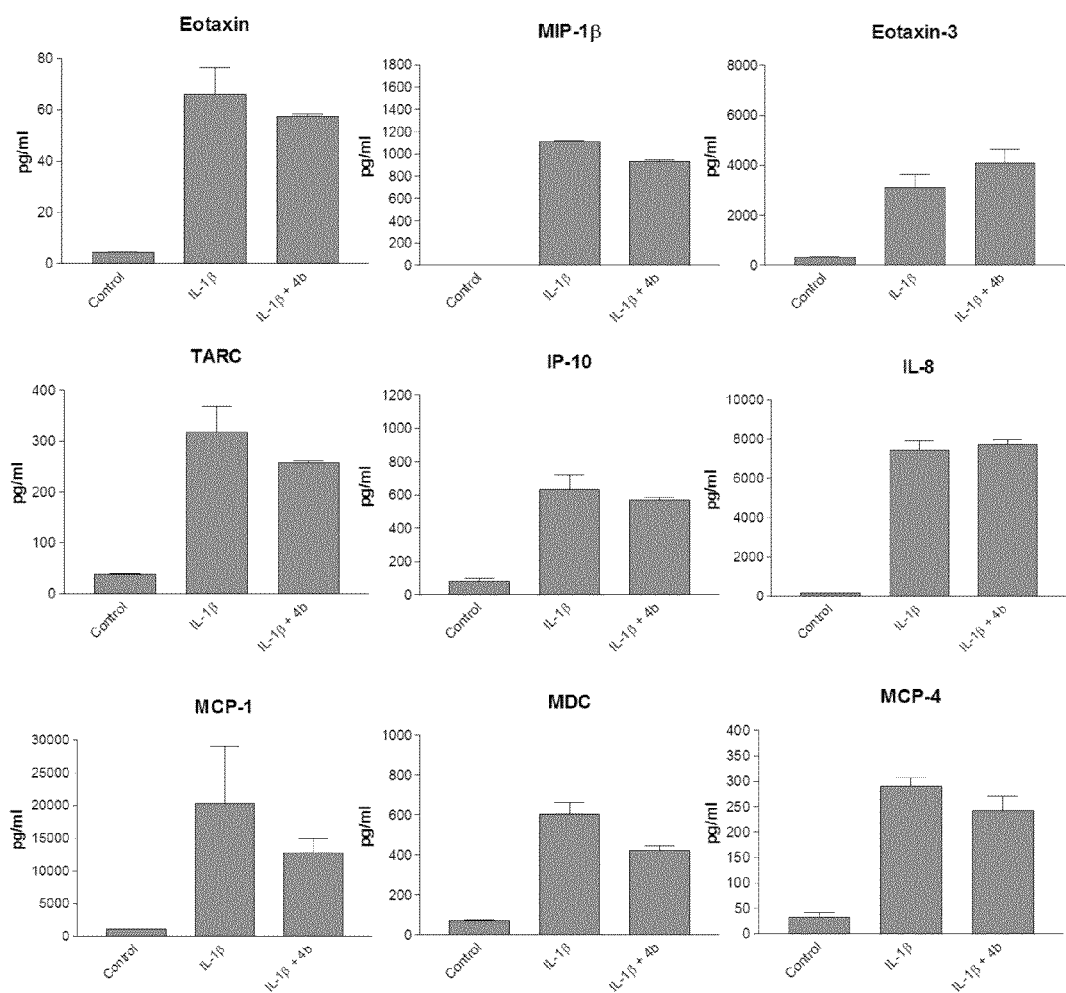
FIG. 8 shows the anti-inflammatory activity of compound 4b as determined by chemokine release profiles in A549 cells stimulated with IL-1β.
Figure 9:
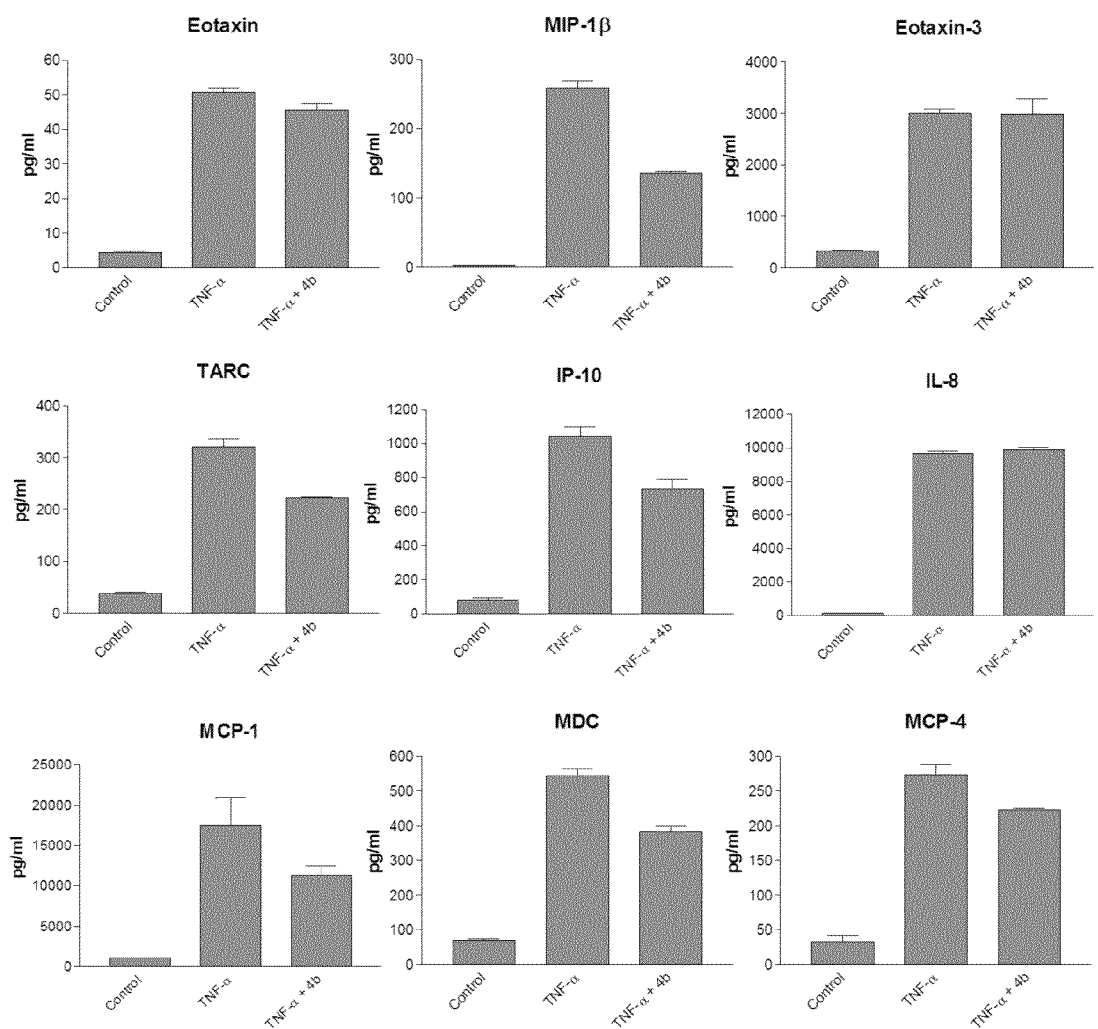
FIG. 9 shows the anti-inflammatory activity of compound 4b as determined by chemokine release profiles in A549 cells stimulated with TNF-α.
Figure 10:
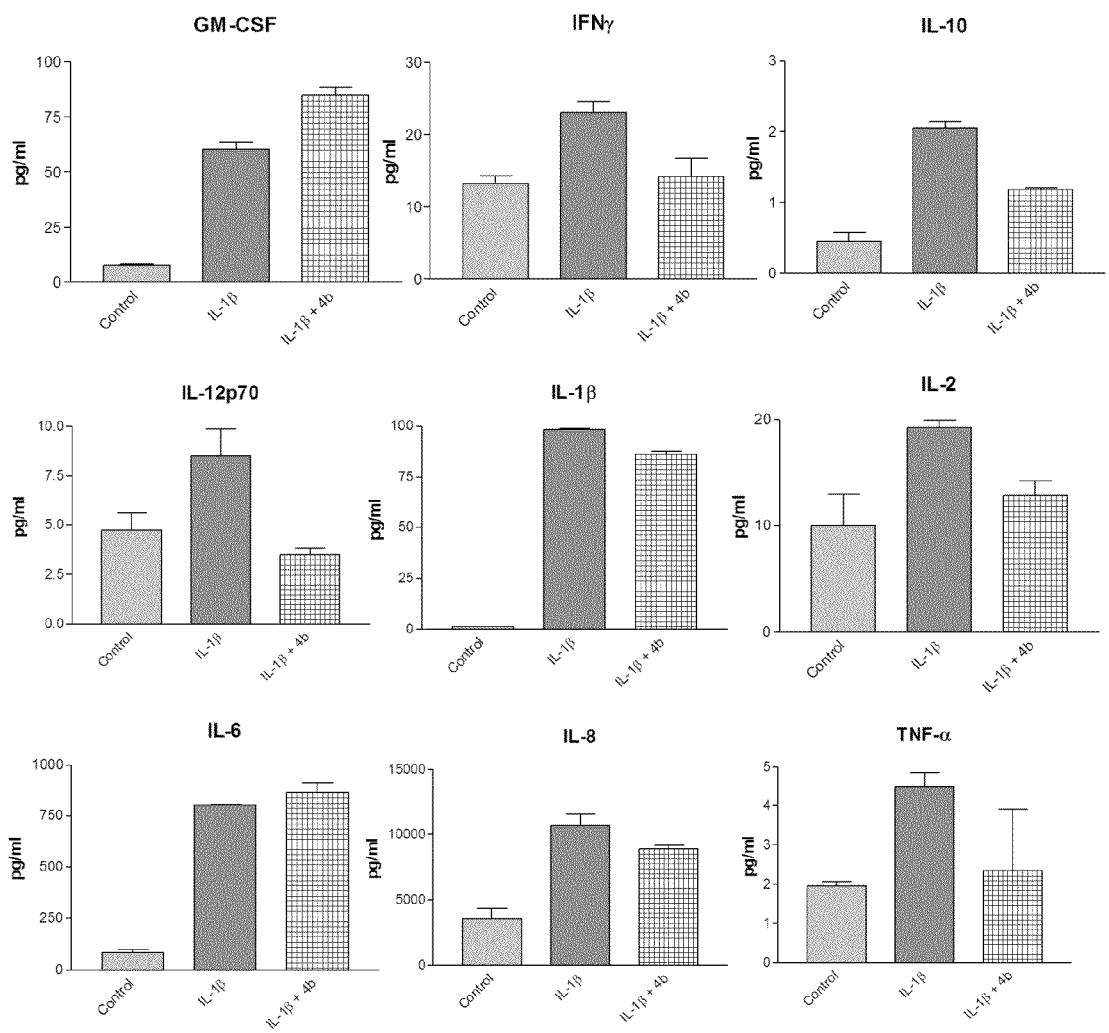
FIG. 10 shows the anti-inflammatory activity of compound 4b as determined by cytokine release profiles in HUVEC cells stimulated with IL-1β.
Figure 11:
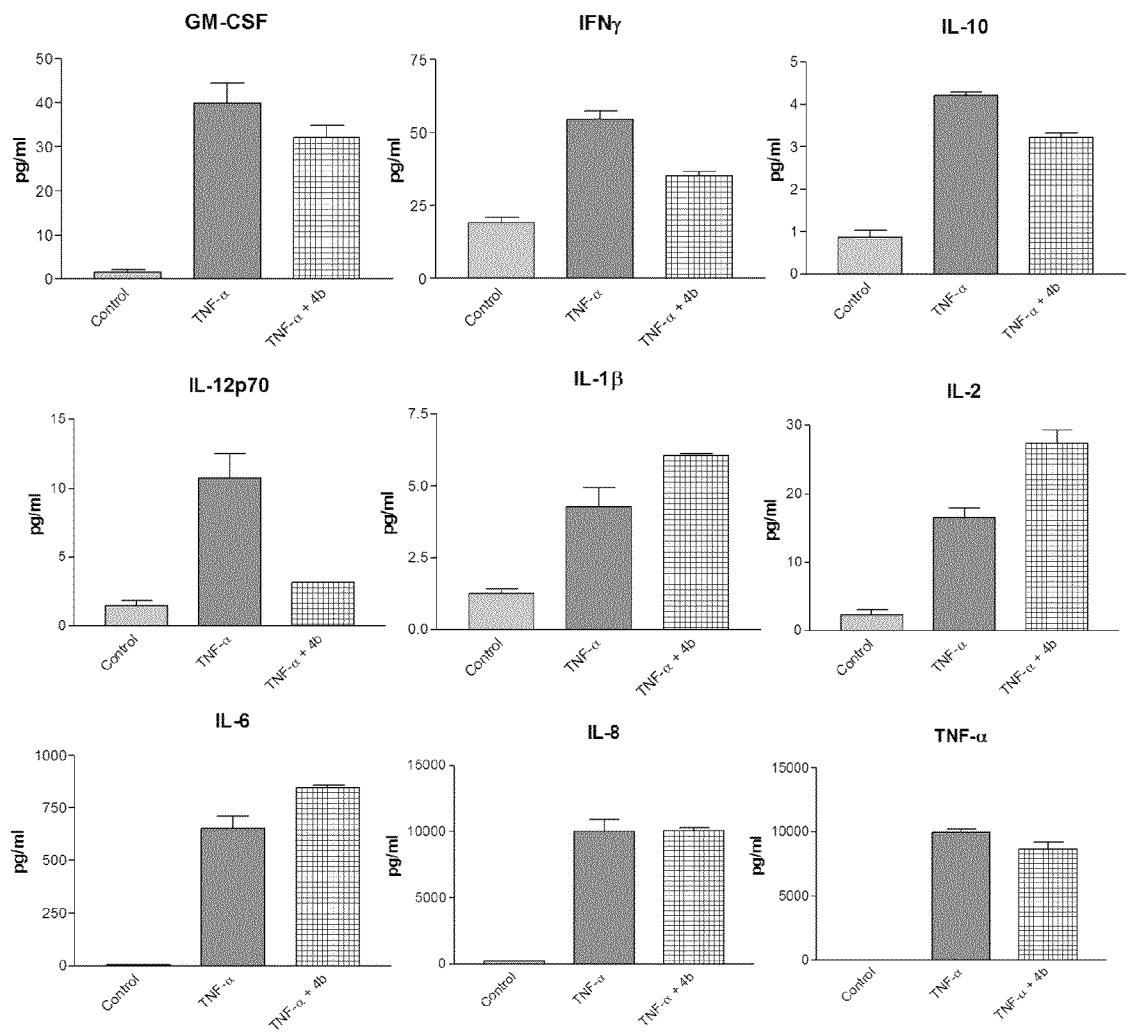
FIG. 11 shows the anti-inflammatory activity of compound 4b as determined by cytokine release profiles in HUVEC cells stimulated with TNF-α.
Figure 12:
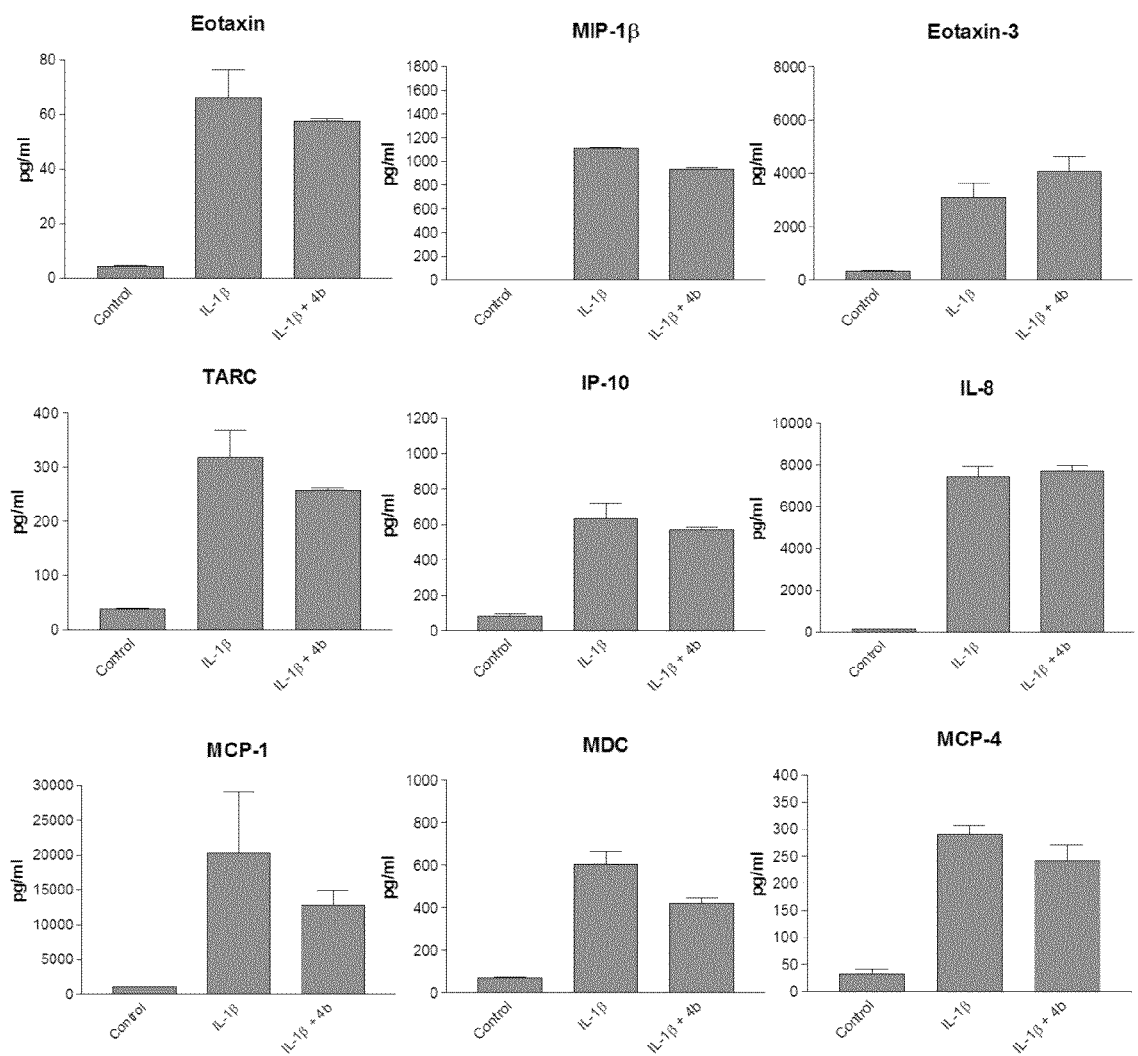
FIG. 12 shows the anti-inflammatory activity of compound 4b as determined by chemokine release profiles in HUVEC cells stimulated with IL-1β.
Figure 13:
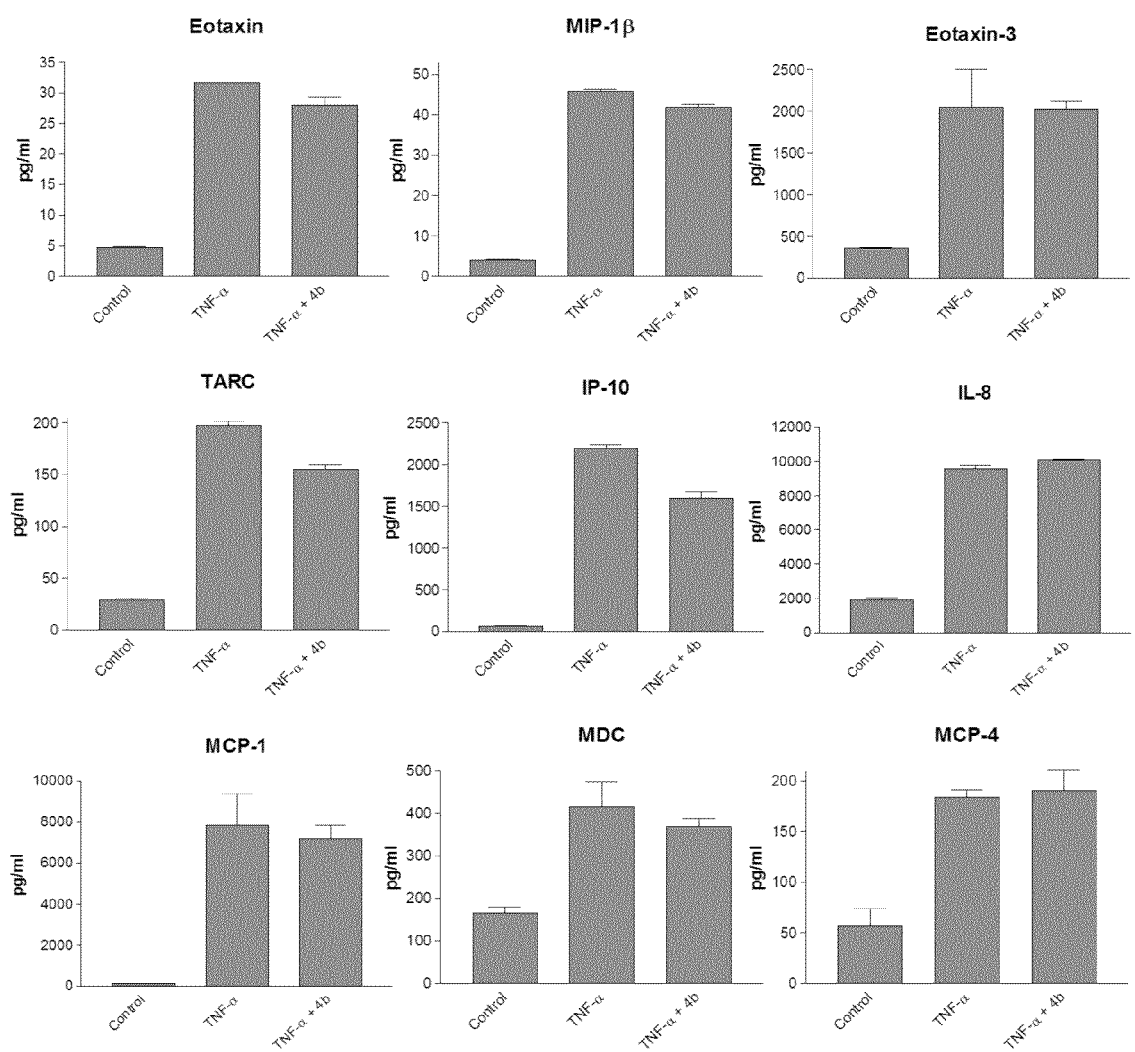
FIG. 13 shows the anti-inflammatory activity of compound 4b as determined by chemokine release profiles in HUVEC cells stimulated with TNF-α.

FIGS. 1 and 2 depict the functional activity of compound 4c at the CB-1 and CB-2 receptor, respectively.

Cytoxocity assay: Cells are seeded on a 96 well polystyrene plate in full serum media at a density of 75,000 cells per milliliter, 100 μL per well. Plates are incubated at 37° C. and 5% $CO_2$ for 24 hours to allow cell attachment. Drug solutions are prepared in DMSO at 100× concentration and mixed 1:100 in 1% FBS media to yield the desired concentration. Drug-media mixtures are vortexed immediately prior to administration to cells. Full serum media is removed and replaced with drug-media mixtures and incubated for 18 hours. 104 of Cell Counting Kit 8 (CCK8, Dojindo# CK04-11) is added to each well to colormetrically assess viability. After 2-4 hours of incubation with the CCK8 dye, absorbance is read at 450 nm by a BioTek Synergy 2 plate reader.

The cytotoxicity of selected compounds against the glioblastoma brain cancer cell line LN-229 is depicted in Table 1.

TABLE 1

| Compound | $EC_{50}$ LN-229, 48 hrs |
| --- | --- |
| 4c | 33.62 μM |

Differentiation of Monocytes: To THP human leukemia monocytes (ATCC #TIB-202) in suspension is added phorbol 12-myristate 13-acetate (PMA Aldrich #P1585) and ionomycin (Aldrich #I0634), 10 and 500 ng/ml respectively, to induce differentiation into macrophage-like cells. Cells are seeded at 30,000 cells/well in a 96-well polystyrene dish and allowed to incubate at 37° C. in 5% CO2/95% air for 5-10 days to complete transformation. Media is refreshed as needed until assay.

Cytokine and Chemokine Assays: A549 (ATCC #CCL-185), HUV-EC-C (ATCC #CRL-1730), or differentiated THP-1 cells are maintained according to suppliers recommendations and are seeded on 96-well polystyrene plates at a density of 300,000 cells/ml (100 μL per well) and incubated at 37° C. in 5% CO2/95% air for 24 hours to allow cell attachment. Drug solutions are prepared in DMSO at 100× concentration and mixed 1:100 in media containing 1% FBS to yield the desired concentration. Plates are then removed from the incubator and the complete growth media is replaced with 50 μL media containing 1% FBS and lipopolysaccharide or peptidoglycan at 1 μg/ml (for differentiated THP-1), or TNF-α (10 ng/ml) or IL-1β (1 ng/ml) in the case of A549 or HUV-EC-C, or without stimulus in the case of control wells. Cells are returned to the incubator for 1 hour before drug treatments. Drug-media solutions are prepared at 2× desired final concentration in media containing 1% FBS and the appropriate stimulus at the previously mentioned concentration. Control media is also prepared which contained only vehicle (DMSO). 50 μL of media containing drug or vehicle alone is then added to appropriate wells and the plates returned to the incubator for 18 hours. Media supernatants are then assayed for cytokines and chemokines using the Human ProInflammatory 9-PlexTissue Culture Kit (MSD # K15007B-1) and the Human Chemokine 9-PlexTissue Culture Kit (MSD # K15001B-1) according to the manufacturer's protocol. The plates are then imaged on the SECTOR Imager 2400 (Meso Scale Discovery) according to the manufacturer's instructions.

FIGS. 3-13 show the anti-inflammatory activity of compound 4b as determined by cytokine release profiles in THP-1 cells stimulated with LPS.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims.

What is claimed is:

1. A compound of the formula

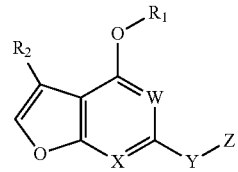

wherein
one of W and X can be N and the other can be C;
Y is selected from the group consisting of S, O, $CH_2$, $CH(CH_3)$, $CH(OH)$, $C(CH_3)(OH)$, $C(CH_3)_2$, $C(-U(CH_2)_nU-)$, $C((CH_2)_nCH_3)_2$, $C(O)$, NH, $S(O)$, $S(O)_2$, $S(O)NH$ and $S(O)_2NH$;
U is selected from the group consisting of $CH_2$, S, and O;
n is an integer from 1 to 6;
Z is selected from the group consisting of alkyl, cycloalkyl, and
  aryl, heteroaryl, and arylalkyl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl;
$R_1$ is selected from the group consisting of H, $CH_3$, $CH_2CH_3$, aminoalkyl, morpholinoalkyl, and hemisuccinate; and
$R_2$ is selected from the group consisting of H,
  alkyl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl,
  cycloalkyl, aryl, heteroaryl and heterocycloalkyl optionally substituted with up to five groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl, and
  arylalkyl, cycloalkylalkyl, heterocycloalkylalkyl and heteroarylalkyl, wherein the ring portion is optionally substituted with up to five groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl, and
  pharmaceutically acceptable salts thereof.

2. A compound according to claim 1 wherein $R_2$ is selected from the group consisting of phenyl and thiophenyl optionally substituted with up to five groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl.

3. A compound according to claim 1 wherein $R_1$ is selected from H, alkyl, aminoalkyl, morpholinoalkyl, and hemisuccinate.

4. A compound according to claim 1 wherein Y is selected from the group consisting of carbonyl, sulfonyl, dimethylmethylene and hydroxymethylene.

5. A compound according to claim 1 wherein Z is selected from the group consisting of alkyl, phenyl, cycloalkyl and thiophenyl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl.

6. A compound according to claim 5 wherein Z is selected from the group consisting of alkyl, phenyl, thiophenyl and cycloalkyl.

7. A compound according to claim 4 wherein Y is selected from the group consisting of dimethylmethylene or carbonyl.

8. A compound according to claim 1 wherein
$R_2$ is selected from the group consisting of phenyl and thiophen-2-yl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl;
$R_1$ is selected from the group consisting of hydrogen, methyl and ethyl;
Y is selected from the group consisting of $C(O)$, $S(O)_2$, $CH_2$, $CH(CH_3)$, $CH(OH)$, $C(CH_3)(OH)$ and $C(CH_3)_2$; and
Z is selected from the group consisting of alkyl, phenyl, thiophen-2-yl and cyclohexyl optionally substituted with up to three groups independently selected from a group consisting of alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl.

9. A compound according to claim 8 wherein Y is $C(CH_3)_2$.

10. A compound according to claim 9 wherein $R_1$ is hydrogen.

11. A compound according to claim 1 selected from the group consisting of
a) 6-(2-methyloctan-2-yl)-3-m-tolylfuro[2,3-b]pyridin-4-ol;
b) 3-(3,5-dichlorophenyl)-6-(2-methyloctan-2-yl)furo[2,3-b]pyridin-4-ol;
c) 6-(2-methyloctan-2-yl)-3-phenylfuro[2,3-b]pyridin-4-ol;
d) 6-(2-methyloctan-2-yl)-3-(thiophen-2-yl)furo[2,3-b]pyridin-4-ol;
e) 3-(3,5-dimethoxyphenyl)-6-(2-methyloctan-2-yl)furo[2,3-b]pyridin-4-ol;
f) 6-(2-cyclohexylpropan-2-yl)-3-m-tolylfuro[2,3-b]pyridin-4-ol;
g) 6-(2-cyclohexylpropan-2-yl)-3-(3,5-dichlorophenyl)furo[2,3-b]pyridin-4-ol;
h) 6-(2-cyclohexylpropan-2-yl)-3-phenylfuro[2,3-b]pyridin-4-ol;
i) 6-(2-cyclohexylpropan-2-yl)-3-(thiophen-2-yl)furo[2,3-b]pyridin-4-ol;
j) 5-(3,5-dichlorophenyl)-2-(2-(thiophen-2-yl)propan-2-yl)furo[2,3-d]pyrimidin-4-ol;
k) 3-phenyl-6-(2-phenylpropan-2-yl)furo[2,3-b]pyridin-4-ol; and
l) 6-(2-phenylpropan-2-yl)-3-(thiophen-2-yl)furo[2,3-b]pyridin-4-ol.

12. A pharmaceutical composition comprising a compound of claim 1, or a salt thereof, and a pharmaceutically acceptable carrier component.

13. A method of treating brain cancer or inflammation comprising contacting a cannibinoid receptor with a compound in an amount to treat said brain cancer or inflammation, wherein the compound is of the formula

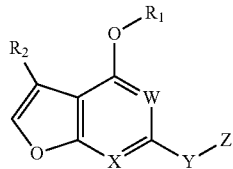

wherein
one of W and X can be N and the other can be C;
Y is selected from the group consisting of S, O, $CH_2$, $CH(CH_3)$, $CH(OH)$, $C(CH_3)(OH)$, $C(CH_3)_2$, $C(—U(CH_2)_nU—)$, $C((CH_2)_nCH_3)_2$, $C(O)$, $NH$, $S(O)$, $S(O)_2$, $S(O)NH$ and $S(O)_2NH$;
U is selected from the group consisting of $CH_2$, S, and O;
n is an integer from 1 to 6;
Z is selected from the group consisting of alkyl, cycloalkyl, and
aryl, heteroaryl, and arylalkyl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl;
$R_1$ is selected from the group consisting of H, $CH_3$, $CH_2CH_3$, aminoalkyl, morpholinoalkyl, and hemisuccinate; and
$R_2$ is selected from the group consisting of H,
alkyl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl,
cycloalkyl, aryl, heteroaryl and heterocycloalkyl optionally substituted with up to five groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl, and
arylalkyl, cycloalkylalkyl, heterocycloalkylalkyl and heteroarylalkyl, wherein the ring portion is optionally substituted with up to five groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl, and
pharmaceutically acceptable salts thereof.

14. A method according to claim 13 wherein
$R_2$ is selected from the group consisting of phenyl and thiophen-2-yl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl;
$R_1$ is selected from the group consisting of hydrogen, methyl and ethyl;
Y is selected from the group consisting of $C(O)$, $S(O)_2$, $CH_2$, $CH(CH_3)$, $CH(OH)$, $C(CH_3)(OH)$ and $C(CH_3)_2$; and
Z is selected from the group consisting of alkyl, phenyl, thiophen-2-yl and cyclohexyl optionally substituted with up to three groups independently selected from a group consisting of halo, alkyl, alkoxy, hydroxyl, aryl, heteroaryl, cycloalkyl, heterocycloalkyl, cyano, nitro, amino, alkylamino, dialkylamino, thiol, alkylthiol, trifluoromethyl, carboxy, alkylcarboxy and carbamoyl.

15. A method according to claim 14 wherein Y is $C(CH_3)_2$.
16. A method according to claim 15 wherein $R_1$ is hydrogen.
17. A method according to claim 16 wherein the compound is selected from the group consisting of
a) 6-(2-methyloctan-2-yl)-3-m-tolylfuro[2,3-b]pyridin-4-ol;
b) 3-(3,5-dichlorophenyl)-6-(2-methyloctan-2-yl)furo[2,3-b]pyridin-4-ol;
c) 6-(2-methyloctan-2-yl)-3-phenylfuro[2,3-b]pyridin-4-ol;
d) 6-(2-methyloctan-2-yl)-3-(thiophen-2-yl)furo[2,3-b]pyridin-4-ol;
e) 3-(3,5-dimethoxyphenyl)-6-(2-methyloctan-2-yl)furo[2,3-b]pyridin-4-ol;
f) 6-(2-cyclohexylpropan-2-yl)-3-m-tolylfuro[2,3-b]pyridin-4-ol;
g) 6-(2-cyclohexylpropan-2-yl)-3-(3,5-dichlorophenyl)furo[2,3-b]pyridin-4-ol;
h) 6-(2-cyclohexylpropan-2-yl)-3-phenylfuro[2,3-b]pyridin-4-ol;
i) 6-(2-cyclohexylpropan-2-yl)-3-(thiophen-2-yl)furo[2,3-b]pyridin-4-ol;
j) 5-(3,5-dichlorophenyl)-2-(2-(thiophen-2-yl)propan-2-yl)furo[2,3-d]pyrimidin-4-ol;
k) 3-phenyl-6-(2-phenylpropan-2-yl)furo[2,3-b]pyridin-4-ol; and
l) 6-(2-phenylpropan-2-yl)-3-(thiophen-2-yl)furo[2,3-b]pyridin-4-ol.

* * * * *